United States Patent [19]

Sall et al.

[11] Patent Number: 5,484,772
[45] Date of Patent: Jan. 16, 1996

[54] ANTITHROMBOTIC AGENTS

[75] Inventors: Daniel J. Sall; Robert T. Shuman, both of Greenwood; Gerald F. Smith; Michael R. Wiley, both of Indianapolis, all of Ind.

[73] Assignee: Eli Lilly and Company, Indianapolis, Ind.

[21] Appl. No.: 318,325

[22] Filed: Oct. 5, 1994

Related U.S. Application Data

[63] Continuation-in-part of Ser. No. 206,550, Mar. 4, 1994, abandoned.

[51] Int. Cl.$^6$ .............................. A61K 38/00; C07K 5/00; C07K 7/00; C07K 17/00
[52] U.S. Cl. ................ 514/18; 514/19; 530/331; 548/122; 548/123; 548/124; 548/125; 548/950; 546/208; 544/359; 544/333; 540/467; 540/470
[58] Field of Search ..................... 548/122–125, 548/950; 546/208; 544/141, 586, 372, 359; 540/467, 470; 530/331; 514/18, 19

[56] References Cited

U.S. PATENT DOCUMENTS

| | | |
|---|---|---|
| 4,316,889 | 2/1982 | Bajusz et al. . |
| 4,346,078 | 8/1982 | Bajusz et al. . |
| 4,399,065 | 8/1983 | Bajusz et al. . |
| 4,478,745 | 10/1984 | Bajusz et al. . |
| 4,703,036 | 10/1987 | Bajusz et al. ............... 514/18 |
| 5,053,392 | 10/1991 | Klein et al. ................. 514/18 |
| 5,153,176 | 10/1992 | Abe et al. ................... 514/18 |
| 5,202,416 | 4/1993 | Steuber et al. ............. 530/322 |
| 5,204,323 | 4/1993 | Findlay et al. ............. 514/2 |
| 5,250,660 | 10/1993 | Shuman et al. ............ 530/344 |
| 5,252,566 | 10/1993 | Shuman et al. ............ 514/210 |

FOREIGN PATENT DOCUMENTS

| | | |
|---|---|---|
| 0293881 | 12/1988 | European Pat. Off. . |
| 0410411 | 1/1991 | European Pat. Off. . |
| 0479489 | 4/1992 | European Pat. Off. . |
| 0526877 | 8/1992 | European Pat. Off. . |
| 0503203 | 9/1992 | European Pat. Off. . |
| 0530167 | 3/1993 | European Pat. Off. . |
| 0529568 | 3/1993 | European Pat. Off. . |
| 0542525 | 5/1993 | European Pat. Off. . |
| WO93/08211 | 4/1993 | WIPO . |
| WO93/11152 | 6/1993 | WIPO . |
| WO93/15756 | 8/1993 | WIPO . |

OTHER PUBLICATIONS

Bajusz, S., et al., *J. Med. Chem.*, 1990, 33, 1729–1735.
Fareed, J., et al., *Annals N.Y., Academy of Sciences*, 1981, 765–784.
Shuman, et al., Proceedings of the Twelfth American Peptide Symposium, Jun. 16–21, 1991, pp. 799–802.
Wilson, et al., American Heart Association, Nov. 11–14, 1991, Anaheim Convention Center, Anaheim, Calif., Abstract.
Bajusz, et al., *Int. J. Peptide Res.*, 12, 1978, 217–221.
Gesellchen, et al., Tenth American Peptide Symposium, May 23–28, 1987, St. Louis, Mo.
Claeson, et al., Proceedings of the Twelfth American Peptide symposium, Jun. 16–21, 1991, Cambridge, Mass., pp. 824–825.
Smith, G. F., Shuman, R. T. Gesellchen, P. D., Craft, T. J., Gifford, P., Kurz, K. D., Jackson, C. V. Sandusky, G. E. and P. D. Williams, A New Family of Thrombin Inhibitors with Improved Specificity and Therapeutic Index. (Submitted to the American Heart Association, Oct. 1991, Circulation Oct., 1991, vol. 84, II–579, 1991, Abstract.
Jackson, V., Wilson, H., Frank, J., Crowe, V., Craft, T., and G. Smith. The Thrombin Inhibitor, Methyl–D–Phe–Pro–Arginal–An Effective Adjunct to Coronary Artery Thrombolysis in the Anesthetized Dog. FASEB J, 5(4)A520 (1991).
Crowe, V., Frank, J., Wilson, H., Coffman, B., Smith, G., and V. Jackson. Anticoagulant and Antithrombotic Efficacy of the Novel Thrombin Inhibitor Methyl–D–Phg–Pro–Arginal in a Canine Model of Coronary Thrombosis. FASEB J. 594)A520 (1991).
Wilson, H., Frank, J., Crowe, V., Coffman, B., Smith, G., Shuman, R., and V. Jackson. Anticoagulant and Antithrombotic Efficacy of the Novel Thrombin Inhibitor, Methyl–D–Phg.–Pro–Arginal, in a Canine Model of Coronary Thrombosis (Arteriosclerosis and Thrombosis, II(5), Oct., 1991) p. 1586a.
Jackson, V., Wilson, H., Frank, J, Crowe, V., Coffman, B., Shuman, R., and G. Smith. The Novel Thrombin Inhibitor Methyl–D–Phg–Pro–Arginal: An Effective Conjunctive Agent to Coronary Artery Thrombolysis in the Anesthetized Dog. (Arterioscloerosis and Thrombosis, II(5), Oct., 1991 p. 1586a.
Shuman, R. T., Rothenberger, R. B., Campbell, C. S., Smith, G. F., Jackson, C. V., Kurz, K. D., and P. D. Gesellchen. Prevention of Reocclusion by a Thrombin Inhibitor. (American Peptide Symposium, Jun., 1991, pp. 799–800).
Shuman, R. T., Rothenberger, R. B., Campbell, C. S., Smith, G. F., Jackson, C. V., Kurz, K. D., and P. D. Gesellchen. A Series of Highly Active Serine Proteinase Inhibitors. (American Peptide Symposium, Jun. 1991, pp. 801–802.
Jackson, C. V., Frank, J. D., Crowe, V. G., Craft, T. J., and G. F. Smith. Assessment of the Anticoagulant and Antithrombotic Efficacy of the Thrombin Inhibitor, BOC–Phe–Pro Arginal, in a Canine Model of Coronary Thrombosis. *Arterioscleросis*, 10922A (1990).
Jackson, C. V., Frank, J. D., Crowe, V. G., Craft, T. J., and G. F. Smith. The Thrombin Inhibitor, BOC–D–Phe–Pro–Arginal. An Effective Adjunct to Coronary Artery Thrombolysis in the Anesthetized Dog. *Arteriosclerosis, l 10923a (1990).*

(List continued on next page.)

*Primary Examiner*—Jill Warden
*Assistant Examiner*—Sheela J. Huff
*Attorney, Agent, or Firm*—Thomas E. Jackson; David E. Boone; John C. Demetery

[57] ABSTRACT

This invention relates to L-arginine aldehyde derivatives, pharmaceutical formulations containing those compounds and methods of their use as thrombin inhibitors, coagulation inhibitors and thromboembolic disorder agents.

55 Claims, No Drawings

OTHER PUBLICATIONS

Shackelford, K. A., Tanzer, R. L., Shuman, R., Gesellchen, P. D., Grindley, G. B., Sundboom, J. L., Smith, G. F., and R. L. Merriman. Inhibition of Spontaneous Metastasis by Boc–D–Phe–Pro–Arginal. American Association for Cancer Research, San Francisco, 1989, *Proc. Am. Assn. Cancer Res.*, 30 86, 1989.

Neubauer, B. L., Clemens, J. A., Gesellchen, P. D., Hirsch, K. S., Hoover, D. M., Merriman, R. L., and G. F. Smith. Endocrine Characterization and Sensitivity of the PAIII Prostatic Adenocarcinoma in Male Lobund–Wistar(LW) Rats to Anti–Fibrin Agents. American Association for Cancer Research. New Orleans, May 1988, *Proc. Am. Assn. Cancer Res.* 29 240 (1988).

Neubauer, B. L., Best, K. L., Gesellchen, P. D., Goode, R. L., Merriman, R. L., Tanzer, L. R., Shaar, C. J., Shuman, R., Sundbloom, Pro–Arginal on the Metastasis of the PAIII Prostatic Adenocarcinoma in Male Lobund Wistar (LW) Rats. American Urological Association. Boston, May 1988, *J. Urol.*, 139 175A (1988).

Gesellchen, P. D., Smith, G. F., et al., Anticoagulant, Antithromboric, and Antimetastatic Effects of A Serine Proteinase Inhibitor. 10th American Peptide Symposium. Washington University, St. Louis, Mo. (1987), Abstract.

Smith, G. F., Sundboom, J. L., Best, K., Gesellchen, P. D., Merriman, R. L., Shuman, R., and Neubauer, B. L., Heparin, Boc–D–Phe–Pro–Arginal, and Warfarin (Fibrin Antagonists) Inhibit Metastasis in an In Vivo Model. American Chemical Society National Meeting. Abstract BIOL 70 Biochemistry (1987).

K. D. Kurz, T. Smith, R. A. Moore, and B. W. Main. Comparison of Thrombin Inhibitors in Rat Models of Thrombosis and Thrombolysis. FASEB Journal, vol. 5(No. 4), 1991. Abstract #886.

Tomori, et al., *Chromatographia*, vol. 19, 437–442 (1984).

Dayhoff, *Atlas of Protein Sequence and Stucture*, 5, pp. 85–89 (1972).

Shuman, et al, *J. Med. Chem.*, 36(3), 314–319 (1993).

Jackson, et al., *J. Cardiovasc, Pharmacol.*, 21(4), 587–594 (1993).

Cheng, et al., *Tetrahedron Lett.*, 32 (49), 7333–7336 (1991).

Bagdy, et al., *Thrombosis and Haemostasis*, 68(2), 125–129 (1992).

*Thrombosis and Haemostasis*, 65, 1289, Nos. 2150–2151 and 2152 (1991).

Bagdy, et al., *Thrombosis and Haemostasis*, 67(3), 325–330 (1992).

Bagdy, et al., *Thrombosis and Haemostasis*, 67(3), 357–365 (1992).

Balasubramanian, et al., *J. Med. Chem.*, 36, 300–303 (1903).

Shuman, et al., Oral Activity of Tripeptide Aldehyde Thrombin Inhibitors, Thirteenth American Peptide Symposium, Jun. 20–25, 1993, Abstract.

Kurz et al., Antithrombotic Efficacy in the Rat After Intravenous and Oral Administration of a Direct Inhibitor of Thrombin FASEB, Mar. 28–Apr. 1, 1993.

Iwanowicz, et al, *Bioorg. Med. Chem. Lett.*, 2(12). 1607–1612 (1992).

Barabas, et al., *Blood Coagul. Fibrin.*, 4, 243–248 (1993).

Jackson, et al., Conjunctive Therapy with the Thrombin Inhibitor, LY 294468, and Aspirin Produced Enhanced Antireocclusive Activity When Used in a Canine Model of Streptokinase–Induced Coronary Thrombolysis, *The Pharmacologist*, 35(3), 207 (1993), Abstract #407.

Pozagay, et al., Study of the Specificity of Thrombin with Tripeptidyl–p–Nitroanilide Substrates, *Eur. J. Biochem.*, 115, 491–495 (1981).

5,484,772

ANTITHROMBOTIC AGENTS

This is a continuation-in-part of application Ser. No. 08/206,550, filed Mar. 4, 1994 now abandoned.

BACKGROUND OF THE INVENTION

This invention relates to thrombin inhibitors which are useful anticoagulants in mammals. In particular it relates to L-arginine aldehyde derivatives having high anticoagulant activity, antithrombotic activity, and thrombin selectivity.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation is currently achieved by the administration of heparins and coumarins.

Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin mime (APTT) assay). Coumarins impede the generation of thrombin by blocking the post-translational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest in small synthetic peptides that are recognized by proteolytic enzymes in a manner similar to that of natural substrates has grown. Tripeptide aldehydes such as D-Phe-Pro-Arg-H, Boc-D-Phe-Pro-Arg-H, and D-MePhe-Pro-Arg-H, Bajusz et al., *J. Med. Chem.*, 33, 1729–1735 (1990) demonstrate potent direct inhibition of thrombin. Many investigators have synthesized analogs in an effort to develop pharmaceutical agents, for example Shuman et al., *J. Med. Chem.*, 36, 314– 319 (1993).

Although the heparins and coumarins are effective anticoagulants, and no drug has yet emerged from the known tripepride aldehydes, and despite the continuing promise for this class of compounds, there exists a need for anticoagulants that act selectively on thrombin, and independent of antithrombin III, exert inhibitory action shortly after administration, and do not interfere with lysis of blood clots, as required to maintain hemostasis.

The present invention is directed to the discovery that the compounds of the present invention, as defined below, are potent, selective thrombin inhibitors.

Accordingly, it is a primary object of the present invention to provide novel L-arginine aldehyde derivatives that are potent thrombin inhibitors useful as anticoagulants.

Other objects, features, and advantages will be apparent to those skilled in the art from the following description and claims.

SUMMARY OF THE INVENTION

The present invention provides thrombin inhibiting compounds having the formula $$Y-\overset{O}{\underset{||}{C}}-X-\underset{|}{\overset{H}{N}}-\overset{*}{C}H-(CH_2)_3-\underset{|}{\overset{H}{N}}-\overset{NH}{\underset{||}{C}}-NH_2 \quad I$$
$$\underset{|}{C=O}$$
$$\underset{|}{R^1}$$

where $R^1$ is hydrogen;

X is prolinyl or azetidinyl-2-carbonyl;

Y is a group $$R^3-\underset{|}{\overset{Z}{\underset{|}{C}}}-\\ \underset{|}{Z^1}\\ R^4$$

where Z is hydroxy, $C_1$–$C_4$ alkoxy or —$NHR^2$;

$R^2$ is hydrogen, $C_1$–$C_6$ alkyl, cyclopentyl, cyclohexyl, a group $$-\overset{O}{\underset{||}{C}}-R^5$$

or —$S(O)_n$—$R^5$ where $R^5$ is $C_1$–$C_4$ alkyl, $C_1$–$C_2$ perfluoroalkyl, $C_1$–$C_4$ alkoxy, ($C_1$–$C_4$ alkoxy)$C_1$–$C_4$ alkyl, cyclopentyl, cyclohexyl, amino, mono ($C_1$–$C_4$)alkylamino, di($C_1$–$C_4$) alkylamino, unsubstituted or substituted aryl, where aryl is phenyl or naphthyl, a 5 or 6 member unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

n is 1 or 2;

$R^3$ is $C_1$–$C_4$ alkyl, unsubstituted or substituted phenyl or unsubstituted or substituted benzyl;

$Z^1$ is a bond or —$CH_2$—;

$R^4$ is $C_1$–$C_6$ alkyl, $C_1$–$C_4$ alkoxy, cyclopentyl, cyclohexyl, unsubstituted or substituted aryl where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted bicyclic heterocyclic group having one or two heteroatoms which are the same or different and which are selected from sulfur, oxygen and nitrogen;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted bicyclic hydrocarbyl group; and pharmaceutically acceptable salts and solvates thereof;

provided that when (a-i) $R^3$ is methyl or ethyl; $Z^1$ is a bond; $R^4$ is cyclopentyl, cyclohexyl, unsubstituted or substituted aryl where aryl is phenyl or naphthyl or $R^4$ is thienyl or furyl; and X is prolinyl or azetidinyl-2-carbonyl; or (a-ii) $R^4$—$Z^1$— taken together form methyl or ethyl; $R^3$ is unsubstituted or substituted phenyl; and X is prolinyl or azetidinyl-2-carbonyl; or when (b-i) $R^3$ is methyl or ethyl; $Z^1$ is —(CH$_2$)—; $R^4$ is unsubstituted or substituted phenyl; and X is azetidinyl-2-carbonyl; or (b-ii) $R^4$—$Z^1$— taken together form methyl or ethyl; $R^3$ is unsubstituted or substituted benzyl; and X is azetidinyl-2-carbonyl; or further when (c) $R^3$ and $R^4$ are taken together to afford a cyclopentyl or cyclohexyl; and X is prolinyl;

then Z is not hydroxy, $C_1$–$C_4$ alkoxy or $NHR^2$ in which $R^2$ is hydrogen, $C_1$–$C_6$ alkyl or a group

in which $R^5$ is $C_1$–$C_4$ alkyl, $C_1$–$C_2$ perfluoroalkyl or $C_1$–$C_4$ alkoxy.

A particular group of compounds of the above formula I consists of those compounds of formula I where
$R^1$ is hydrogen;
X is prolinyl or azetidinyl-2-carbonyl;
Y is a group

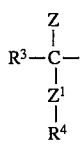

where $R^3$ is $C_1$–$C_4$ alkyl;
$Z^1$ is a bond or —CH$_2$—;
$R^4$ is unsubstituted or monosubstituted phenyl; and
Z is —$NHR^2$, where
$R^2$ is

in which $R^5$ is a 9 or 10 membered unsubstituted or monosubstituted fused bicyclic heterocyclic group having one nitrogen atom; or $R^2$ is a group —SO$_2$R$^5$ in which $R^5$ is $C_1$–$C_4$ alkyl; or $R^3$ and Z are taken together to afford an azetidinyl group, or a 5 or 6 membered unsubstituted heterocyclic ring having one or two nitrogen atoms; and pharmaceutically acceptable salts and solvates thereof.

In addition to the compounds of formula I, the present invention provides pharmaceutical formulations comprising a compound of formula I in association with a pharmaceutically acceptable carrier, diluent or excipient.

The present invention also provides a method of inhibiting coagulation in mammals comprising administering to a mammal in need of treatment, a coagulation inhibiting dose of a compound of formula I.

The present invention further provides a method of inhibiting thrombin comprising administering to a mammal in need of treatment, a thrombin inhibiting dose of a compound of formula I.

Further, the present invention provides a method of treating thromboembolic disorders comprising administering to a mammal requiring treatment, an effective dose of a compound of formula I.

DETAILED DESCRIPTION OF THE INVENTION

This invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

The term "alkyl" by itself or as part of another substituent means a straight or branched chain alkyl radical having the stated number of carbon atoms such as methyl, ethyl, n-propyl, isopropyl, n-butyl, t-butyl, isobutyl and sec-butyl.

The term "alkoxy" means a straight or branched chain alkyl radical having the stated number of carbon atoms bonded to the parent moiety by an oxygen atom. The term "halo" means chloro, fluoro, bromo or iodo.

The term "di($C_1$–$C_4$ alkyl)amino" means a group —N($C_1$–$C_4$ alkyl)$_2$ where each alkyl group, independently, has the stated number of carbon atoms.

The term "perfluoroalkyl" means a straight or branched chain alkyl radical having the stated number of carbon atoms with all available valences substituted with fluoro atoms such as trifluoromethyl and pentafluoroethyl.

The term "5 or 6 membered heterocyclic ring" means any 5 or 6 membered ring that will afford a stable structure containing one or two nitrogen atoms; one sulfur atom; one oxygen atom; one nitrogen and one sulfur atom; or one nitrogen and one oxygen atom. The 5-membered ring has one or two double bonds and the 6-membered ring has two or three double bonds. Heterocyclics include furyl, thienyl, pyrrolyl, pyrazolyl, oxazolyl, isoxazolyl, thiazolyl, isothiazolyl, pyranyl, pyridinyl, pyrimidinyl, pyrazinyl, oxazinyl and thiazinyl.

The term "9 or 10 membered heterocyclic ring" means any fused bicyclic heterocyclic group in which any of the above 5 or 6 membered rings is fused to a benzene ring a cyclohexane ring, or another 6 membered heterocyclic ring, as defined above, that will afford a stable structure. These heterocyclics include indolyl, benzothienyl, benzofuryl, benzoxazolyl, benzoisoxazolyl, benzopyrazolyl, quinolinyl, isoquinolinyl, benzimidazolyl and benzothiazolyl.

The term "9 or 10 membered bicyclic hydrocarbyl group" means a fused bicyclic group

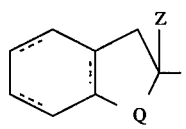

where Q is —CH$_2$—, —CH=CH— or —CH$_2$—CH$_2$—;
Z is as shown and defined above for Formula I; and the dotted lines mean the presence or absence of unsaturation in the ring.

Representative examples of these fused bicyclic groups include indanyl, dihydronaphthyl and tetrahydronaphthyl.

The groups

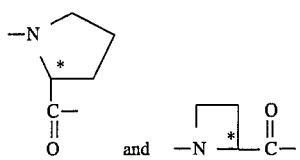

are referred to as prolinyl and azetidine-2-carbonyl, respectively, and are respectively abbreviated Pro and Azt.

In the representation of Formula I, the carbonyl functionality of x is attached to the amino group drawn in Formula I.

It will be appreciated that many of the above heterocycles may exist in tautomeric forms. All such forms are included within the scope of this invention.

All of the above aryl, heterocycles, and bicyclic hydrocarbyls are unsubstituted or substituted with one or two substituents that will afford a stable structure independently selected from halo, hydroxyl, $C_1$–$C_4$ alkyl, $C_1$–$C_4$ alkoxy, amino (—$NH_2$), (mono($C_1$–$C_4$ alkyl) amino, mercapto, and ($C_1$–$C_4$ alkyl)thio (—$S(O)_p C_1$–$C_4$ alkyl), —$NHS(O)_p(C_1$–$C_4$ alkyl), $NHC(O)C_1$–$C_4$ alkyl, —$S(O)_p NH_2$, —$S(O)_p NH(C_1$–$C_4$ alkyl), and —$S(O)_p N(C_1$–$C_4)$ alkyl)$_2$, where p is 0, 1 or 2.

The asterisks in formula I and substituent X denote a chiral center that is (L).

In addition, diastereomers exist at the Y substituent and, depending on substitutions on said Y substituent, further diastereomers may exist. The compounds of the present invention include mixtures of two or more diastereomers as well as each individual isomer.

Preferred compounds of the present invention are those compounds of formula I as defined above where
$R^1$ is hydrogen;
Z is —$NHR^2$, where
$R^2$ is

or —$S(O)_n$—$R^5$;
$R^3$ is $C_1$–$C_4$ alkyl;
$R^4$ is unsubstituted or substituted aryl where aryl is phenyl or naphthyl;
$R^5$ is $C_1$–$C_4$ alkyl, $C_1$–$C_4$ alkoxy, a 5 or 6 membered unsubstituted or substituted heterocyclic ring having one or two nitrogen atoms, or a 9 or 10 membered unsubstituted or substituted fused bicyclic heterocyclic group having one or two nitrogen atoms;
n is 1 or 2; or
Z is taken together with $R^3$ to afford an azetidinyl group, a 5 or 6 membered unsubstituted or substituted heterocyclic ring having one or two nitrogen atoms or a 9 or 10 membered unsubstituted or substituted fused bicyclic heterocyclic group having one or two nitrogen atoms;
and where X and $R^1$ are as defined above for formula I and pharmaceutically acceptable salts and solyates thereof.

A first, particularly preferred group of compounds of the present invention are those compounds of formula I as defined above where
$R^1$ is hydrogen;
Z is —$NHR^2$, where
$R^2$ is

$R^3$ is $C_1$–$C_4$ alkyl;
$Z^1$ is —$CH_2$—;
$R^4$ is unsubstituted or monosubstituted phenyl;
$R^5$ is $C_1$–$C_4$ alkoxy, or a 9 or 10 membered unsubstituted or monosubstituted fused bicyclic heterocylic group having one nitrogen atom; and X is as defined above for formula I, and pharmaceutically acceptable salts and solyates thereof.

A second particularly preferred group of compounds of the present invention are those compounds of formula I where
$R^1$ is hydrogen;
Z is —$NHR^2$, where
$R^2$ is —$SO_2R^5$;
$R^3$ is $C_1$–$C_4$ alkyl
$R^4$ is unsubstituted or monosubstituted phenyl;
$R^5$ is $C_1$–$C_4$ alkyl; and X and $Z^1$ are as defined above for formula I, and pharmaceutically acceptable salts and solvates thereof.

A third group of particularly preferred compounds of the present invention are those compounds of formula I where
$R^1$ is hydrogen;
Z is —$NHR^2$;
$R^4$ is unsubstituted or monosubstituted phenyl; and
$R^3$ and Z are taken together to afford an azetidinyl group, or a 5 or 6 membered unsubstituted heterocyclic ring having one or two nitrogen atoms; and X is as defined above for formula I, and pharmaceutically acceptable salts and solvates thereof.

As mentioned above, the invention includes pharmaceutically acceptable salts of the compounds defined by the above formula I. A particular compound of this invention can possess one or more sufficiently basic functional groups, and accordingly react with any of a number of nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and sulfuric acid.

As stated above, the present invention includes solyates of the compounds of Formula I and the pharmaceutically acceptable salts thereof. A particular compound of the present invention or a pharmaceutically acceptable salt thereof may form solvates with water or common organic solvents. Such solvates are included within the scope of compounds of the present invention.

The compounds of formula I are prepared by known methods of peptide coupling. According to one such method the acid PY-COOH, where Y has the same meanings as defined for formula I, and P is an amino protecting group, is coupled with a carboxy protected proline (or azetidine-2-carboxy ester) to form the dipeptide. The carboxy protecting ester group of the proline moiety is then removed (deblocked or deesterified) and the free acid form of the dipeptide is coupled with the lactam form of arginine. The above reaction sequence is illustrated by the following Scheme 1:

PY—COOH + proline ester ———>

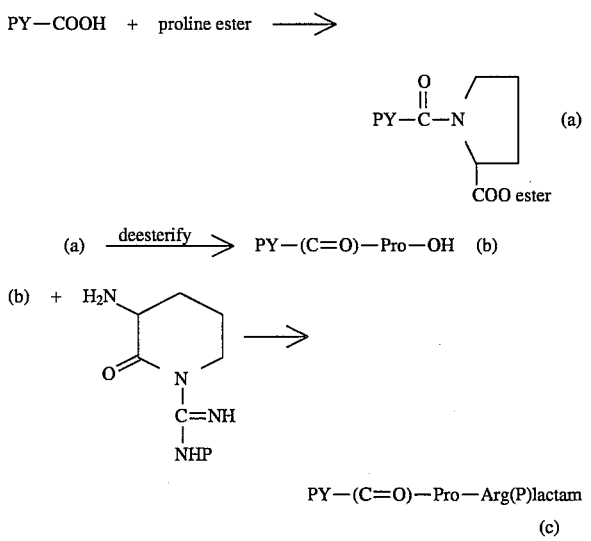

wherein P represents an amino protecting group.

The coupled Arg(P) lactam product (c) is reacted with a hydride reducing agent, preferably lithium aluminum hydride or lithium tri-tert-butoxyaluminohydride, in an inert solvent or mixture of solvents to reduce the lactam ring and provide the tripepride in the arginine aldehyde form represented by the formula

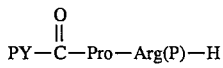

wherein (P) represents amino protecting groups.

The protecting groups are removed by procedures known to those skilled in the art such as hydrogenation over a metal catalyst.

The lactam form of arginine is obtained by intramolecular coupling of amino protected arginine [Arg-OH]. For example, Boc-Arg(Cbz)OH represented by the formula

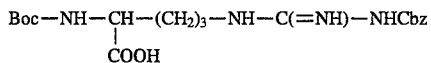

where Boc is t-butyloxycarbonyl and Cbz is benzyloxycarbonyl is first converted to an active ester form, such as an active mixed anhydride, with a chloroformate ester, e.g. ethyl chloroformate to isobutyl chloroformate. The ester formation is carried out in the presence of a tertiary amine such as N-methylmorpholine. Addition of further or another tertiary amine base, such as triethylamine or diisopropyl-ethylamine, effects the internal acylation to provide the lactam form of the diamino protected arginine as shown below

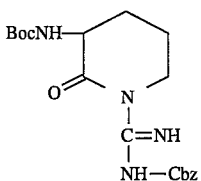

Prior to use in the coupling with the PY(C=O)-Pro-OH as shown in the above scheme, the Boc or other amine protecting group is selectively removed with trifluoroacetic acid or HCl to provide the requisite free amino group.

The coupling of an PYCOOH compound with a proline ester, when Y is as defined above for formula I, is carried out by first protecting the amino group of the amino acid. Conventional amino protecting groups commonly used for temporary protection or blocking of the amino group are employed.

The amino-protecting group refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, t-butoxycarbonyl 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3- chlorobenzyloxycarbonyl, 2- chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, 9-fluoroenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichlorethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group, and the like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the benzyloxycarbonyl, allyloxycarbonyl, t-butyloxycarbonyl, and trityl groups. Similar amino-protecting groups used in the cephalosporin, penicillin and peptide art are also embraced by the above terms. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In carrying out the coupling reaction an ester protecting group for proline is employed which is removable by conditions under which the amino protecting group remains intact. The amino protecting group of the acylating acid PYCOOH thus remains in place for protection of the amino group during the subsequent coupling with the arginine lactam compound to form c.

The carboxy protecting ester group as used in the specification refers to one of the ester derivatives of the carboxylic acid group commonly employed to block or protect the carboxylic acid group while reactions are carried out on other functional groups on the compound. Examples of such carboxylic acid protecting groups include $C_1$-$C_3$ alkyl, benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4''-trimethoxytrityl, 2-phenylprop-2-yl, trimethylsilyl, t-butyldimethylsilyl, phenacyl, 2,2,2-trichloroethyl, 2-(trimethylsilyl)ethyl, 2-(di(n-butyl)methylsilyl)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected molecule to strong nucleophilic bases or reductive conditions employing highly activated metal catalysts such as Raney nickel. (Such harsh removal conditions are also to be avoided when removing amino-protecting groups discussed below.) Preferred carboxy protecting groups are $C_1$-$C_3$ alkyl and benzyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of formula I where X is azetidinyl (or prolinyl) are prepared in an analogous manner by known methods of peptide coupling. According to one such method, the cyclic lactam form of arginine (e) is prepared and coupled with an amino protected azetidine-2-carboxylic acid (d) as shown below to afford the dipeptide (f)

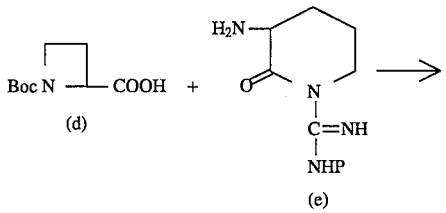

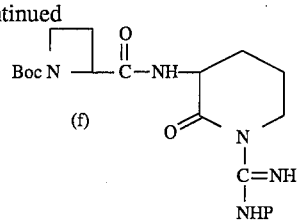

(f)

where P represents an amino protecting group such as the benzyloxycarbonyl (Cbz) group, t-butoxycarbonyl (Boc), p-toluenesulfonyl, and the like. Preferably the amino protecting group used is removable by hydrogenation or treatment with mild acid (e.g. trifluoroacetic acid) or a strong acid (e.g. HCl). Examples of other suitable amino protecting groups are provided in "Protective Groups in Organic Synthesis", Second Edition, by T. W. Greene and Peter G. M. Wuts, Chapter 7, page 309–405 (1991), John Wiley & Sons, Inc., publishers. The Boc, or other suitable protecting group, is removed from the azetidine ring nitrogen which is then acylated with the desired amino acid acyl group to afford the tripepride shown below.

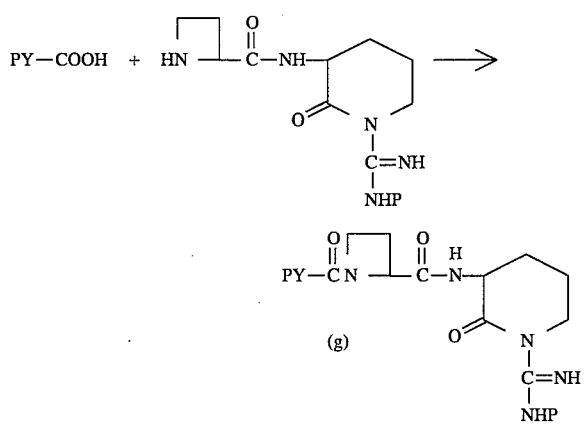

Although illustrated and described for those compounds of the present invention where X is azetidinyl-2-carbonyl, one skilled in the art will appreciate these procedures can also be used to afford those compounds of the present invention where X is prolinyl.

The coupled Arg(P) lactam product (g is reduced with a hydride reducing agent, preferably lithium aluminum hydride or lithium tri-tert-butoxyaluminohydride in an inert solvent or mixture of solvents to reduce the lactam and provide the tripepride in the arginine aldehyde form represented by the formula PY(C=O)-Azt-Arg(P)-H wherein P represents an amino protecting group. The protecting groups are removed by procedures known to those skilled in the art such as hydrogenation over a metal catalyst.

Alternatively, the compounds of the invention are prepared by coupling the PYCOOH acid with carboxy protected 2-azetidine-carboxylic acid. The carboxy is deprotected as the dipeptide which is then coupled with the amino protected arginine in the lactam form prepared as described above. The tripepride is then reduced to provide the amino protected arginal tripeptide as described above.

The coupling of an PYCOOH compound is carried out by first protecting the amino group of the amino acid. Conventional amino protecting groups commonly used for temporary protection or blocking of the amino group are employed. Examples of such protecting groups are described above.

The coupling reactions described above are carried out in the cold preferably at a temperature between about −20° C. and about 15° C. The coupling reactions are carried out in an inert organic solvent such as dimethylformamide, dimethylacetamide, tetrahydrofuran, methylene chloride, chloroform, and like common solvents or a mixture of such solvents. Generally anhydrous conditions are used when, in the coupling reaction, an active ester of the acylating acid is used.

Those compounds of formula I where the Y substituent (α,α-disubstituted amino acids) are not commercially available can be readily prepared by the methods illustrated below in scheme 2. A suitable α-amino ester is condensed with benzophenone imine and the resulting imines are deprotonated with a strong base such as potassium t-butoxide or lithium bis(trimethylsilyl)amide. The resulting carbanions are then treated with an appropriate electrophile such as primary alkylhalides, allylic alkyl halides or benzylic alkyl halides. The imine can then be removed by treatment with aqueous acid (from about 1N to about 3N inorganic acid, preferably HCl) and the resulting amino acid derivative can be carried on to the compounds of formula I as described above.

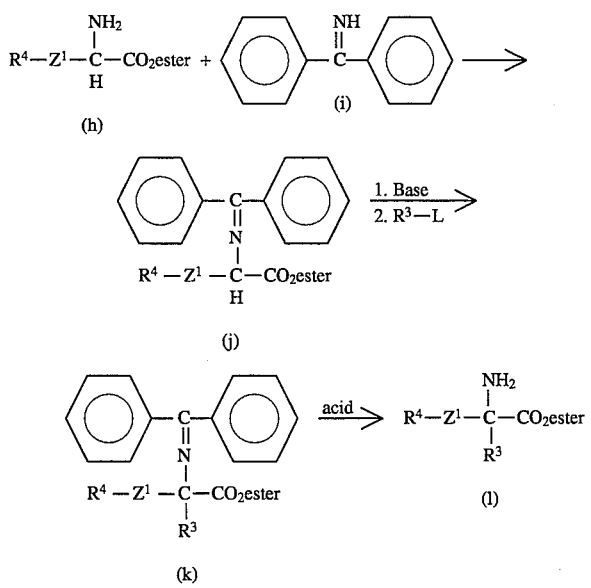

In Scheme 2, $Z^1$, $R^4$ and $R^3$ are as defined for formula I, L is a good leaving group, preferably halo, and "ester" is a suitable carboxy protecting group, preferably $C_1$–$C_4$ alkyl. The compound (1) is further reacted using convential synthetic procedures to afford the desired Z substituent as defined for formula I. Such procedures include blocking the amino group with a suitable protecting group, deblocking the carboxy group and then carrying out coupling to afford the compounds of the present invention as described above.

An α-amino acid ester which is N-substituted (such as Azt) (i.e., those compounds of formula I were Z is —$NHR^2$ and is taken together with $R^3$) can be α-substituted directly, using a strong base (such as lithium diisopropyl amide, LDA) and an electrophile $R^4$-$Z^1$--L, where $R^4$ and $Z^1$ are defined for formula I and L is a good leaving group, preferably halo, provided a nitrogen protecting group (P) is employed which is stable to the basic reaction conditions.

Both of the above procedures for α-substituting an α-amino acid ester afford a mixture of enantiomers which can be separated or carried forward as a racemic mixture.

A further method for preparing suitable α-substituted-α-amino acids (substituent Y of formula I) is by means of the Strecker synthesis. Generally, α-amino nitriles are prepared by the treatment of an aldehyde or ketone with NaCN and $NH_4Cl$. Further details regarding this synthetic method, and variants thereof, are in March, *Advanced Organic Chemistry*, 3rd Ed., John Wiley & Sons, Inc. (1985), pp. 855–856.

The compounds of the invention are isolated best in the form of acid addition salts. Salts of the compounds of formula I formed with acids such as those mentioned above are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalenesulfonic acid may be so used.

The preferred method for purifying the compounds of formula I, while at the same time preparing a desired stable salt form, is that described in U.S. Pat. No. 5,250,660 incorporated by reference herein. According to the method, stable sulfates or hydrochlorides are provided by preparative purification over $C_{18}$ reversed-phase chromatography in which the aqueous component comprises sulfuric acid or hydrochloric acid at pH 2.5 and acetonitrile as the organic component. The pH of the acidic eluant is adjusted to between about pH 4 and about 6 with an anion exchange resin in the hydroxyl form e.g. Bio-Rad AG-1X8. After adjustment of the pH, the solution of tripepride sulfate or hydrochloride salt is lyophilized to provide the pure salt in dry powder form. In an example of the process, crude EtOCO-D-Phe(αMe)-Pro-ArgH·HCl is dissolved in water and the solution is loaded on a Vydac $C_{18}$ RPHPLC column (5 cm×50 cm). A gradient (10 mL/min) of 2 through 20% B (Solvent A=0.05% HCl; Solvent B= acetonitrile) over 280 min, followed by isocratic 20% B through 400 min is used. Multiple fractions are collected and those containing product as determined by analytical RP-HPLC are pooled. The pH of the pooled fractions is adjusted to 4.5 with AG-1X8 resin in hydroxide form (Bio-Rad, 3300 Ragatta Blvd., Richmond, Calif. 94804). The solution is filtered and the filtrate is lyophilized to provide the pure D-,L-,L-, tripeptide in the form of the hydrochloride salt.

The optically active isomers of the diastereomers of the Y substituent are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds employed as initial starting materials in the synthesis of the compounds of this invention are well known and, to the extent not commercially available, are readily synthesized by standard procedures commonly employed by those of ordinary skill in the art.

The following Examples are provided to further describe the invention and are not to be construed as limitations thereof.

The $R_f$ values in the following examples unless otherwise stated, were determined by silica gel thin layer chromatography using Kieselgel 60F-254 (Merck, Darmstadt) in the following solvent systems:

(A) chloroform-methanol-acetic acid, 135:15:1, V:V:V
(B) ethyl acetate-acetic acid-absolute ethanol, 90:10:10, v:v:v
(C) chloroform-methanol-acetic acid, 90:30:5, v:v:v
(D) ethyl acetate The analytical HPLC methods used in the examples were as follows:

Method 1. Waters 600E using a Vydac $C_{18}$ reversed-phase column of 0.46 cm ×10 cm. The chromatogram was monitored on an LDC at 214 nM using a gradient of A= water containing 0.1% (v:v)TFA and B=acetonitrile containing 0.1% (v:v) TFA Method 2. Pharmacia FPLC using a Vydac $C_{18}$ reversed-phase column measuring 0.46 cm ×10.0 cm. Monitoring was done on a Pharmacia UV-M at 214 nM using a gradient of either A=water containing 0.1% (v:v) TFA or B =acetonitrile containing 0.1% (v:v) TFA.

Method 3- Hitachi L-6200 using a Vydac $C_{18}$ reversed-phase column of 0.46 cm ×10 cm. Samples were eluted using a gradient composed of A (0.1% (v:v) aqueous TFA) and B (0.1% (v:v) TFA in acetonitrile). The chromatogram was monitored at 214 nm using a L-4000 UV detector.

The abbreviations used in the examples have the following meanings.

Amino acids: Arg=arginine, Pro=proline, Azt=azetidine-2-carboxylic acid

Boc=t-butyloxycarbonyl (t-butoxycarbonyl)
Bzl=benzyl
Cbz=benzyloxycarbonyl
DCC=dicyclohexylcarbodiimide
DMF=dimethylformamide
DMSO=dimethylsulfoxide
EtOAc=ethyl acetate
$Et_2O$=diethyl ether
EtOH=ethanol
FAB-MS=fast atom bombardment mass spectrum
FD-MS=field desorption mass spectrum
HOBT=1-hydroxybenzotriazole hydrate
HPLC=High Performance Liquid Chromatography
IR=Infrared spectrum
LAH=lithium aluminum hydride
NMR=nuclear magnetic resonance
NMI=N-methylindole-2-carbonyl
Phg=phenylglycine
RPHPLC=Reversed Phase High Performance Liquid Chromatography
TFA=trifluoroacetic acid
THF=tetrahydrofuran
TLC=thin layer chromatography
OPFF=pentafluorophenoxy
PFF=pentafluorophenyl Unless otherwise stated, pH adjustments and work up are with aqueous acid or base solutions. RPHPLC is carried out using 0.05% aqueous (v:v) HCl (designated "A" in the Examples) and acetonitrile (designated "B" in the Examples). Mixtures of A and B are v:v. Where $^1$H-NMR is shown, the product afforded by the reaction was characterized by proton NMR to confirm the desired compound was obtained.

EXAMPLE 1

Preparation of 1-methylindole-2-Carbonyl-D-(α-methyl)phenylglycine-Azt-Arg-H hydrochloride A) Boc-Arg(Cbz)-OH To a solution of Boc-Arg(HCL)-OH (82.1 g, 250 mmole) in 5N NaOH (240 ml) chilled to −5° C. was added benzylchloroformate (143 ml, 1.0 mole) (4 eq.) dropwise over 55 minutes while the pH was maintained at 13.2–13.5 using 5N NaOH (250 ml) was added. The aqueous layer was separated and extracted with $Et_2O$ (2×500 ml). The aqueous layer was acidified to pH 3.0 with 3N $H_2SO_4$ (560 ml) and extracted with EtOAc (550 ml). The organic layer separated and aqueous layer extracted with an additional amount of EtOAc. The combined organic layers were washed with water, dried ($MgSO_4$), and concentrated to dryness in vacuo to give the title compound (66.1 g, 65 percent yield):
TLC $R_f$ (C) 0.43;
FD-MS 408 ($M^+$);
$^1$H NMR ($CDCl_3$) δ1.42 (s, 9H), 1.61–1.91 (m, 4H), 3.23–3.41 (m,2H), 4.17 (d, 1H), 5.21 (s,2H), 5.62 (d,1H), 7.30–7.42 (m, 6H), 8.27 (m, 1H).

B) Boc-Arg(Cbz)-lactam

To a solution of Boc-Arg(Cbz)-OH (A) (66.0 g, 0.162 mole) in dry THF (230 ml), cooled to −10° C., was added N-methylmorpholine (18.7 ml, 1.05 eq) followed by isobutylchloroformate (22.5 ml, 1.05 eq). The reaction was stirred 5 minutes at −10° C. and triethylamine (23.5 ml, 1.05 eq) was added. After the reaction was stirred for one hour at −10° C. and one hour at room temperature the reaction was poured into 1 L of ice-water. The resulting precipitate was filtered, washed with cold water, and dried in vacuo. The product was crystallized from EtOAc to give the title compound as a white solid (38.05 g. 60 percent yield):
TLC $R_f$ (A) 0.77;
FD-MS 391 ($MH^+$);
$^1$H NMR ($CDCl_3$) δ1.48 (S,9H), 1.78–1.98 (m,2H), 2.50 (m, 1H), 3.41 (m, 1H), 4.43 (m, 1H), 4.90 (m, 1H), 5.16 (s, 2H), 5.27 (m, 1H), 7.28–7.45 (m, 6H), 9.41 (m, 1H), 9.68 (m, 1H).

C) HCl·Arg(Cbz)-lactam

A solution of HCl(g) saturated in EtOAc (7.2 L) was added dropwise over 30 minutes to a solution of Boc-Arg(Cbz)-lactam (B) (641 g, 1.64 mol) dissolved in $CH_2Cl_2$ (3 L) at −10° C. The reaction was allowed to stir one hour at −10° C. and slowly warmed to room temperature (3 hours). Diethyl ether (12 L) added and the precipitate was filtered, washed with diethyl ether, and dried in vacuo to give the title compound (580 g):
TLC $R_f$ (C) 0.29;
FD-MS 291 ($MH^+$).

D) Methyl-N$^\alpha$diphenylmethylene-DL-phenylglycinate

To a solution of benzophenone imine (53.8 g, 297 mmol) in methylene chloride (500 mL) at room temperature was added DL-phenylglycine methylester hydrochloride (59.9 g, 297 mmol) and the reaction stirred for 48 hours. The reaction mixture was washed 3 times with water (200 mL) and the organic layer was separated, dried ($MgSO_4$), filtered, and concentrated in vacuo to give a clear oil. The oil was crystallized from pentane to give the title compound (98.5 g, 100 percent yield)
FAB-MS 330 ($MH^+$);
Analysis Calculated for $C_{22}H_{19}NO_2$; C 80.22 H 5.81 N 4.25
Found: C 80.50 H 5.93 N 4.14

E) Methyl-N$^\alpha$diphenylmethylene-DL-(α-methyl) phenylglycinate

A solution of methyl-N$^\alpha$diphenylmethylene-DL-phenylglycinate (D) (14.8 g, 44.8 mmol) in anhydrous THF (200 mL) was added dropwise to a mixture of 18-crown-6 (11.8 g, 44.8 mmol), potassium hydride (11.2 g, 67.3 mmol), THF (100 mL) under an inert atmosphere. To the reaction was added a solution of methyl iodide (6.0 mL, 89.7 mmol) in THF (20 mL) dropwise. The reation was stirred for an additional 1.5 hours at room temperature. To the reaction was added a solution containing D, HOAc (7.0 mL), water (25 mL), and THF (30 mL) dropwise. The reaction was diluted with ethyl acetate and water, the organic layer was separated, washed three times with water, dried (MgSO$_4$), and filtered. The filtrate was concentrated in vacuo to give an oil which crystallized from hexane to give the title compound (10.2 g, 66 percent yield)

FAB-MS 344 (MH$^+$)

Analysis Calculated for C$_{23}$H$_{21}$NO$_2$; C 80.44 H 6.15 N 4.08
Found: C 80.40 H 6.26 N 4.03

F) DL-($\alpha$-methyl)phenylglycine

A solution of methyl-N$^\alpha$diphenylmethylene-DL-($\alpha$-methyl)phenylglycinate (E) (72.4 g, 211 mmol) in 5N HCl (400 mL) was refluxed (24 hours). The solution was cooled to room temperature, filtered, and the filtrate pH adjusted to 5.8 with dilute NH$_4$OH solution. The aqueous solution concentrated in vacuo until crystallization began. The reaction stored overnight at 5° C. and the precipatate filtered, and dried in vacuo to give the title compound (22 g, 63 percent yield)

FAB-MS 166 (MH$^+$).

G) D-($\alpha$-methyl)phenylglycine

A solution of DL-($\alpha$-methyl)phenylglycine (F) (87 g, 431.4 mmol) in water was adjusted to pH 6.0 with 5N NaOH. The precipitate was filtered and dried to yield 82 g of white solid. The solid (82 g) was suspended in 96 percent formic acid (750 mL) and acetic anhydride (200 mL, 431.4 mmol) was added slowly to the reaction mixture. The reaction was allowed to stir at room temperature for 30 minutes and the solution concentrated in vacuo to an oil. The oil was dissolved in EtOAc (1500 mL), washed three times with water, dried (MgSO$_4$), and filtered. The filtrate was concentrated in vacuo and crystallized from EtOAc/hexane to give a white solid of N$^\alpha$-formyl-DL-($\alpha$-methyl)phenylglycine (77.9 g, 93 percent). The N$^\alpha$-formyl-DL-($\alpha$-methyl)phenylglycine (77.3 g, 400 mmol) was dissolved in EtOAc (450 mL) and EtOH (50 mL). To this solution was added quinine (68.18 g, 210 mmol) and diethylether (1000 mL). The solution was allowed to stand at room temperature (24 hours). The resulting crystalline material was filtered and the mother liquors were concentrated in vacuo to a white solid. The white solid was suspended in EtOAc, washed with 1.5N citric acid, water, dried (MgSO$_4$), and filtered. The filtrate was concentrated in vacuo to a white solid of N$^\alpha$-formyl-D-($\alpha$-methyl)phenylglycine (26.3 g, 67 percent yield); [$\alpha$]$_D$=−61° (C=0.5/MeOH) . The N$^\alpha$-formyl-D-($\alpha$-methyl)phenylglycine (25 g, 124 mmol) was suspended in 2N HCl (130 mL) and the reaction was refluxed (2 hours). The reaction mixture was cooled to room temperature and the aqueous solution concentrated in vacuo until crystallization began. The precipitate was collected and dried in vacuo to give pure title compound (18.6 g, 74 percent yield).

H) 1-methylindole-2-carbonyl-D-($\alpha$-methyl)phenylglycine

To a solution of D-($\alpha$-methyl)phenylglycine (G) (2.01 g, 10 mmol) in water was added 2N NaOH to adjust the pH to 6.5 and the solution was freeze dried. The solid was suspended in DMF (30 mL), bis(trimethylsilyl)acetamide (3.7 mL, 15 mmol), and 1-methylindole-2-carboxylpentafluorophenyl ester (3.41 g, 10 mmol) was added to the reaction.

The reaction mixture was stirred at 60° C. (24 hours) and concentrated in vacuo to an oil. The residue was dissolved in water (100 mL), diethyl ether (50 mL), and the pH adjusted to 9.0 with 2N NaOH. The aqueous layer was separated, EtOAc (150 mL) was added, and the solution was acidified with 5N HCl to pH 2.8. The organic layer separated, dried (MgSO$_4$), filtered, and concentrated in vacuo to an amorphous solid of the title compound (2.27 g, 70 percent yield)

FAB-MS 323 (MH$^+$).

I) 1-methylindole-2-carbonyl-D-($\alpha$-methyl)phenylglycine-Azt-OH

To a solution of 1-methylindole-2-carbonyl-D-($\alpha$-methyl)phenylglycine (H) (2.2 g, 6.9 mmol) in EtOAc (25 mL) was added 2,4,5 trichlorophenol (1.65 g, 8.3 mmol), DCC (1.72 g, 8.3 mmol), and cooled to 0° C. The reaction was stirred for one hour at 0° C. and 1.5 hours at room temperature. The resultant precipitate was removed by filtration, and the mother liquor was concentrated in vacuo to an oil. The resultant oil was dissolved in pyridine (35 30mL), and L-azetidine-2-carboxylic acid (0.7 g, 6.9 mmol), and triethylamine (0.97 mL, 6.9 mmol) were added to the reaction mixture. After the reaction was stirred at room temperature (24 hours) the pyridine was removed in vacuo to an oil. The residue was dissolved in water (100 mL), diethyl ether (50 mL) and the pH of the solution was adjusted to 9.0 with 2N NaOH. The aqueous layer separated, EtOAc (150 mL) was added, and the pH of the solution adjusted to 3.0 with 3N HCl. The organic layer separated, dried (MgSO$_4$), filtered, and the filtrate evaporated in vacuo to an amorphous solid of crude title compound (2.3 g). The crude solid (2.3 g) was purified by chromatography on silica gel using a step gradient elution (CHCl$_3$ 100 to CHCl$_3$-MeOH 70:30) to yield pure title compound as an amorphous solid (0.81 g, 29 percent yield);

FD-MS 406 (MH$^+$).

J) 1-methylindole-2-carbonyl-D-($\alpha$-methyl)phenylglycine-Azt-Arg(Cbz)-lactam In flask 11-methylindole-2-carbonyl-D-($\alpha$-methyl)phenylglycine-Azt-OH (I) (0.51 g, 1.5 mmol) was dissolved in DMF (10 mL), cooled to −15° C., and N-methylmorpholine (0.17 mL, 1.55 mmol) was added followed by isobutylchloroformate (0.19 mL, 1.41 mmol). The reaction mixture was stirred at −15° C. for 2 minutes. In flask 2 HCl·Arg(Z)-lactam (C) (0.46 g, 1.41 mmol) was dissolved in DMF (10 mL), cooled to 0° C., and diisopropylethylamine (0.27 mL, 1.55 mmol) was added. The reaction mixture was stirred at 0° C. for 2 minutes.

The contents of flask 2 were added to flask 1, and the reaction mixture was stirred for 4 hours (−15° C.) followed by 24 hours at room temperature. A solution of 1 N NaHCO$_3$ (2 mL) was added, and the reaction mixture concentrated in vacuo. The residue was dissolved with EtOAc (100 mL) and water (50 mL). The organic layer was separated and washed sequentially with 1N NaHCO$_3$, water, and 0.1N HCl. The organic layer was dried (MgSO$_4$), filtered, and evaporated in vacuo to an amorphous solid of title compound (0.88 g, 92 percent yield).

TLC R$_f$(A) 0.74;

FAB-MS 678 ( MH$^+$).

K) 1-methylindole-2-carbonyl-D-($\alpha$-methyl)phenylglycine-Azt-Arg-H·HCl

To a stirred, cooled (−70° C.) solution of 1-methylindole-2-carbonyl-D-($\alpha$-methyl)phenylglycine-Azt-Arg(Cbz)-lactam (J) (0.81 g, 1.19 mmol) under a nitrogen atmosphere in anhydrous THF (50 mL) was added lithium aluminum hydride 1M in THF (1.2 mL, 1.2 mmol). The reaction stirred for 30 minutes at −70° C. A solution of 5 mL of THF and 5 mL of 0.5N H₂SO₄ was added dropwise to the reaction. The reaction was diluted with EtOAc (100 mL) and water (50 mL). The organic layer was separated, dried (MgSO₄), filtered, and concentrated to dryness in vacuo to give an amorphous solid (0.76 g). The solid was dissolved in ethanol (100 mL), water (25 mL), and 1N HCl (1.67 mL, 1.67 mmol), and was hydrogenated in the presence of 5 percent Pd/C catalyst (0.5 g) at ambient temperature and pressure. After the reaction was completed, the catalyst was removed by filtration. The filtrate was concentrated to 100 mL in vacuo and freeze dried. The white solid was dissolved in water, filtered through a Millipore 0.5 μm filter, and freeze dried to give pure title compound (0.445 g, 64 percent yield): FAB-MS 546 (MH⁺);
[α]$_D$=−42.9° (=0.5/0.01N HCl).

EXAMPLE 2

Preparation of D-Prolinyl-(αbenzyl)-L-prolinyl-L-arginine Aldehyde, Dihydrochloride Dihydrate

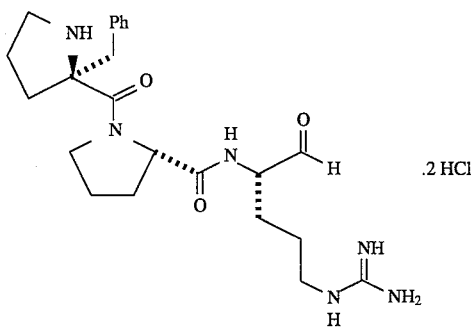

A) N-Cbz-Pro-OMe

To a solution of N-Cbz-proline (140 g, 562 mmol) in methanol (850 mL) was added p-toluenesulfonic acid monohydrate (5 g, 26 mmol). The solution was heated to reflux and stirring continued for 12 h. The heating mantle was removed, and after cooling to room temperature, the solvent was removed by rotary evaporation. The residue was dissolved in ethyl acetate (500 mL), and washed twice with saturated aqueous NaHCO₃ (300 mL), twice with brine (200 mL), dried with MgSO₄, filtered and concentrated to give a colorless oil (129 g, 88% yield)
FD-MS, m/e 263 (M⁺)
Analysis Calculated for C₁₄H₁₇NO₄; C 63.87, H 6.51, N 5.32;
Found: C 64.03, H 6.56, N 5.28.

B) N-Cbz-D,L-Pro-(αbenzyl)-OMe

To a 0.5M solution of potassium hexamethyldisilazide (200 mL, 100 mmol) in toluene at −78° C. and under N₂, was added a solution of N-Cbz-Pro-OMe in tetrahydrofuran (150 mL) via an addition funnel over 1 h. To this mixture was then added a solution of benzyl bromide (11.9 mL, 100 mmol) in tetrahydrofuran (50 mL), via another addtion funnel over 15 min. The cold bath was removed after stirring for 20 h, 1N citric acid (100 mL) was added. The solution was then concentrated to a volume of about 100 mL in vacuo and then partitioned between ethyl acetate (300 mL) and water (200 mL). The organic phase was then washed with 1N citric acid (200 mL), twice with saturated aqueous NaHCO₃, twice with brine, dried with MgSO₄, filtered and concentrated in vacuo to give an amber oil. The oil was then chromatographed over silica gel, eluting with a gradient from hexanes through 20% ethyl acetate/hexanes. The product containing fractions as judged by TLC were combined and concentrated to give a colorless oil (26.9 g, 76% yield).
¹H-NMR C) N-Cbz-D,L-Pro-(αbenzyl)-OH To a solution of N-Cbz-D,L-Pro-(αbenzyl)-OMe (26.9 g, 76 mmol) in p-dioxane (200 mL) was added a solution of LiOH·H₂O (12.8 g, 304 mmol) in water (100 mL). The solution was heated to reflux and stirring continued for 12 h. The heating mantle was then removed and after cooling to room temperature, the solvents were removed by rotary evaporation. The residue was dissolved in water (300 mL) and washed with diethyl ether (200 mL). The aqueous phase was then acidified with 1N citric acid and then extracted three times with diethyl ether (300 mL). The combined ether extracts were dried with MgSO₄, filtered and concentrated to give a white solid (23.9 g, 92% yield).
¹H-NMR
FD-MS, m/e 340 (MH⁺)
Analysis Calculated for C₂₀H₂₁NO₄; C 70.78, H 6.24, N 4.13;
Found: C 71.00, H 6.38, N 4.17.

D) N-Cbz-D-Pro-(αbenzyl)-Pro-OMe

To a solution of N-Cbz-D-Pro-(αbenzyl)-OH (23 g, 68 mmol), Pro-OMe·HCl (14 g, 85 mmol), 1-hydroxybenzotriazole (11.4 g, 85 mmol), and N,N-diisopropylethylamine (35.4 mL, 203 mmol) in dichloromethane (400 mL) was added 1-(3-dimethylaminopropyl)-3-ethylcarbodiimide hydrochloride (16.2 g, 85 mmol). After stirring for 12 h, the solvent was removed in vacuo. The residue was dissolved in ethyl acetate (500 mL) and washed twice with 1N citric acid (200 mL), twice with saturated aqueous NaHCO₃, and twice with brine. The ethyl acetate was removed by rotary evaporation to give a yellow oil. The oil was chromatographed, eluting with a solvent gradient from hexanes through 30% ethyl acetate/hexanes. The fractions containing the higher R$_f$ diastereomer only (TLC, R$_f$ 0.38, 10:1 chloroform:methanol) were combined and concentrated to give a white crystaline solid (10.5 g, 34%). Subsequently, the structure and stereochemistry of this diastereomer was proven to be N-Cbz-D-Pro-(αbenzyl)-Pro-OMe by single crystal X-ray diffraction analysis.
¹H-NMR,
FD-MS, m/e 450 (M⁺)
Analysis Calculated for C₂₆H₃₀N₂O₅; C 69.31, H 6.71, N 6.22;
Found: C 69.18, H 6.73, N 6.25.

E) N-Cbz-D-Pro-(αbenzyl)-Pro-OH

To a solution of N-Cbz-D-Pro-(αbenzyl)-Pro-OMe (8 g, 17.8 mmol) in p-dioxane (200 mL) was added a solution of LiOH·H₂O (3 g, 71 mmol) in water (100 mL) with vigorous stirring. After 12 h, the solution was concentrated to a volume of 50 mL in vacuo, diluted with water (100 mL), and extracted twice with diethyl ether (150 mL). The aqueous phase was adjusted to pH 2 with 5N aqueous HCl and the resulting precipitate was filtered, washed with water and dried to give a white solid (4.2 g, 54% yield). The combined aqueous phase was extracted twice with ethyl acetate (250 mL) and the resulting organic phase was washed with brine (200 mL), dried with Na₂SO₄, filtered, and concentrated to give another 3.2 g (41% yield) of the same product (95% yield combined).
¹H-NMR,
FD-MS, m/e 437 (MH⁺)
Analysis Calculated for C₂₅H₂₈N₂O₅; C 68.79, H 6.47, N 6.42;
Found: C 68.51, H 6.51, N 6.45.

F) D-Pro-(αbenzyl)-Pro-Arg-H·2 HCl

By methods substantially equivalent to those described in example 1-J and 1-K, using LiAi(O-t-Bu)₃H at −23° C. in place of LAH at −78° C., 1.3 g of D-Pro-(αbenzyl)-Pro-Arg-H·2 HCl dihydrate was prepared from N-Cbz-D-Pro-(αbenzyl)-Pro-OH. Purification by RPHPLC was not required.

¹H-NMR,

FAB-MS, m/e 443 (MH⁺)

Analysis Calculated for $C_{23}H_{34}N_6O_3 \cdot 2.5HCl \cdot 2H_2O$; C 48.49, H 7.16, N 14.75;

Found; C 48.84, H 7.05, N 14.48.

EXAMPLE 3

Preparation of Prolinyl (αbenzyl)-L-prolinyl-L-arginine Aldehyde Dihydrochloride

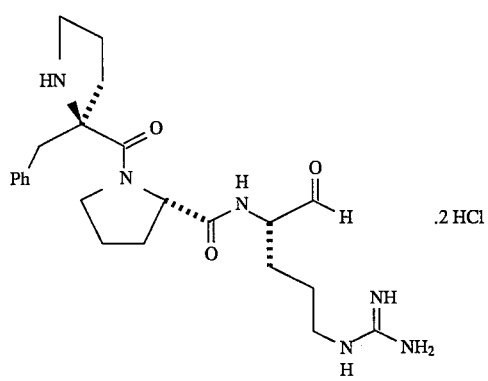

A) N-Cbz-Pro(αbenzyl)-Pro-OMe

N-Cbz-Pro(αbenzyl)-Pro-OMe was prepared in Example 2-D. After silica gel chromatography of the yellow oil, the fractions containing lower $R_f$ material (TLC, $R_f$ 0.31, 10:1 chloroform:methanol) were combined and concentrated to give a white foam (9.6 g, 31% yield), which was assigned by inference to be N-Cbz-Pro-(αbenzyl)-Pro-OMe.

¹H-NMR,

FD-MS, m/e 450 (M⁺)

Analysis Calculated for $C_{26}H_{30}N_2O_5$; C 69.31, H 6.71, N 6.22;

Found: C 69.25, H 6.93, N 6.16.

B) Pro(αbenzyl)-Pro-Arg-H·2 HCl

By methods substantially equivalent to those described in Example 2-E and 2-F, 2.0 g of Pro(αbenzyl)-Pro-Arg-H·2 HCl dihydrate was prepared from N-Cbz-Pro-(αbenzyl)-Pro-OMe. Purification by RPHPLC was not required.

¹H-NMR,

FAB-MS, m/e 443 (MH⁺)

Analysis Calculated for $C_{23}H_{34}N_6O_3 \cdot 3HCl \cdot 2.5H_2O$; C 46.28, H 7.09, N 14.08;

Found: C 46.67, H 7.13, N 13.7 5.

EXAMPLE 4

Preparation of Azetidinyl(αbenzyl)-L-prolinyl-L-arginine Aldehyde Dihydrochloride

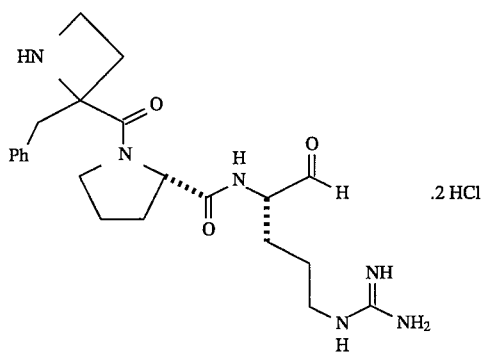

Azt(αbenzyl)-Pro-Arg-H·2 HCl

By methods substantially equivalent to those described in Example 1-A and 2, 1.5 g of Azt(αbenzyl)-Pro-Arg-H-2 HCl was prepared from azetidine-2-carboxylic acid. Purification by RPHPLC was not required.

¹H-NMR,

FAB-MS, m/e 429 ( MH⁺)

Analysis Calculated for $C_{22}H_{32}N_6O_3 \cdot 2.5HCl \cdot 2H_2O$; C 47.55, H 6.98, N 15.12;

Found; C 47.21, H 6.62, N 14.83.

EXAMPLE 5

Preparation Of N-Ethoxycarbonyl-L-phenylalanyl (αmethyl)-L-prolinyl-L-arginine Aldehyde Hydrochloride

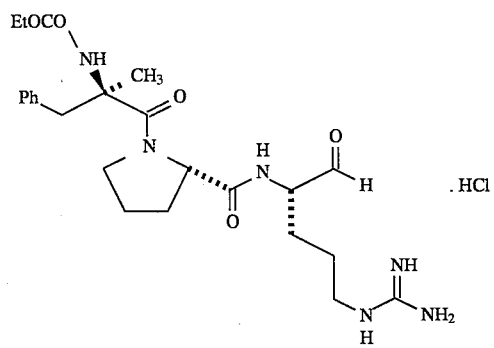

A) EtOCO-D,L-Phe(αMe)-OH

To a stirring suspension of D,L-Phe(αMe)-OH (7.5 g, 42 mmol) in tetrahydrofuran (250 mL) was added N,O-bis(trimethylsilyl)acetamide (12.8 g, 62.8 mmol). Upon clarification the solution was cooled to 0° C. and N,N-diisopropylethylamine (5.4 g, 42 mmol) was added, followed by ethyl chloroformate (4.5 g, 42 mmol). After 2 h, water (100 mL) was added and then the organic solvent was removed in vacuo. The aqueous phase was diluted with 1 N NaOH and washed twice with diethyl ether. The aqueous phase was then acidified to pH 2 with concentrated HCl and extracted three times with ethyl acetate. The combined ethyl acetate extracts were dried ($Na_2SO_4$), filtered and concentrated in vacuo to give 10.3 g (98% yield) of a white solid.

¹H NMR

B) EtOCO-D,L-Phe(αMe)-Pro-OBzl

To a stirring solution of EtOCO-D,L-Phe(αMe)-OH (10.3 g, 41 mmol), HOBT (5.5 g, 41 mmol), Pro-OBzl·HCl (9.9 g, 41 mmol) and N,N-diisopropylethylamine (15.9 g, 123 mmol) in dimethylformamide (200 mL) at 0° C., was added 1-(3-dimethylaminopropyl)-3-ethylcarbodiimide·HCl (8.6 g, 45 mmol). After stirring for 16 h, the solvents were removed in vacuo and the residue was dissolved in ethyl acetate (500 mL). The organic phase was washed three times with 0.1N HCl, three times with saturated aqueous NaHCO$_3$, and once with brine. The organic phase was then dried (Na$_2$SO$_4$), filtered and concentrated in vacuo. The residue was chromatographed over silica gel eluting with 1:1 ethyl acetate:hexanes and the product containing fractions (as judged by TLC) were combined and concentrated in vacuo to give 13.5 g (75% yield) of a white foam.
$^1$H NMR
FD-MS, m/e 438 (M$^+$)
Analysis Calculated for C$_{25}$H$_{30}$N$_2$O$_5$; C 68.47 H 6.90 N 6.39
Found: C 68.20 H 7.09 N 6.28

C) EtOCO-D,L-Phe(αMe)-Pro-OH

To a stirring solution of EtOCO-D,L-Phe(αMe)-Pro-OBzl (13.2 g, 30 mmol) in p-dioxane (250 mL) was added a solution of LiOH·H$_2$O (6.3 g, 151 mmol) in water (125 mL). After stirring for 2.5 h, the solvent was removed in vacuo and the residue was diluted with water and washed three times with diethyl ether. The aqueous phase was then taken to pH 2 with conc. HCl and extracted three times with ethyl acetate. The combined ethyl acetate extracts were dried (Na$_2$SO$_4$), filtered and concentrated in vacuo to give 10.7 g of a white solid.
$^1$H NMR
FD-MS, m/e 349 (MH$^+$)
Analysis Calculated for C$_{18}$H$_{24}$N$_2$O$_5$; C 62.05 H 6.94 N 8.04
Found: C 62.29 H 6.98 N 8.12

D) Boc-Arg(Cbz)-OH

Boc-Arg(HCl)-OH (82.1 g, 250 mmol) was dissolved in 5N NaOH (240 mL) in a 3 necked flask. The reaction mixture was chilled to −5° C. and the pH was maintained at 13.2–13.5 using 5N NaOH (250 mL) while adding benzyl chloroformate (143 mL, 1.0 mol) dropwise (55 min). The reaction mixture was stirred for an additional 1 hour at −5° C. and diluted with water (100 mL) and diethyl ether (500 mL). The aqueous layer was separated and extracted twice with diethyl ether (500 mL). The aqueous layer was then acidified to pH 3.0 with 3N H$_2$SO$_4$ (560 mL) and extracted with ethyl acetate (550 mL). The aqueous layer was separated and extracted once with ethyl acetate. The combined ethyl acetae layers were washed with water, dried (MgSO$_4$) and concentrated in vacuo to give 66.1 g (65% yield) of a white solid:
$^1$H NMR
FD-MS 408 (M$^+$)

E) Boc-Arg(Cbz)-lactam

Boc-Arg(Cbz)-OH (66.0 g, 0.162 mol) was dissolved in tetrahydrofuran (230 mL) and cooled to −10° C. To this solution was added N-methylmorpholine (18.7 mL, 0.17 mol) followed by isobutyl chloroformate (22.5 mL, 0.17 mol). After stirring 5 minutes at −10° C., triethylamine (23.5 mL, 0.17 mol) was added. After an additional 1 hour at −10° C., the mixture was allowed to warm to room temperature and stirring continued for 1 h at room temperature. The reaction mixture was then poured into 1 L of ice-water and the resulting precipitate was filtered, washed with cold water, and dried in vacuo. The product was crystallized from ethyl acetate to give 38 g (60% yield) of a white solid.
$^1$H NMR
FD-MS 391 (MH$^+$)

F) 2HCl·Arg(Cbz)-lactam

A solution of HCl(g) saturated in ethyl acetate (7.2 L) was added dropwise over 30 minutes to a solution of Boc-Arg(Cbz)-lactam (641 g, 1.64 mol) dissolved in dichloromethane (3 L) at −10° C. After 1 h at −10° C. the cold bath was removed and the solution was allowed to warm to room temperature over 3 h. Diethyl ether (12 L) was added and the resulting precipitate was filtered, washed with diethyl ether, and dried in vacuo to give 580 g (97% yield)
FD-MS 291 (MH$^+$)

G) EtOCO-D-Phe(αMe)-Pro-Arg (Cbz) lactam

In flask 1, EtOCO-D,L-Phe(αMe)-Pro-OH ( 6 g, 17.2 mmol) was dissolved in dimethylformamide (100 mL), cooled to − 15° C. and N-methylmorpholine ( 1.7 g, 17.2 mmol) was added, followed by isobutyl chloroformate (2.4 g, 17.2 mmol). The reaction mixture was allowed to stir at −15 ° C. for 10 min.

In flask 2, HCl·Arg(Cbz)lactam (6.3 g, 17.2 mmol) was dissolved in dimethylformamide (100 mL), cooled to 0° C., and N,N-diisopropylethylamine (4.5 g, 34.5 mmol) was added.

The contents of flask 2 were added to flask 1 in one portion and the reaction mixture was allowed to slowly warm to room temperature (24 h). Then saturated aqueous NaHCO$_3$ (100 mL) was added and the solvent was removed in vacuo. The residue was partitioned between ethyl acetate and water and the layers were separated. The organic layer was washed twice with 0.01N HCl, twice with saturated NaHCO$_3$, and once with brine. The organic layer was dried (Na$_2$SO$_4$), and the filtrate was concentrated in vacuo. The residue was chromatographed over silica gel, eluting with ethyl acetate, which provided separation of the diastereomeric products. The fractions containing pure EtOCO-D-Phe(αMe)-Pro-Arg(Cbz)lactam (TLC R$_f$=0.57, 4:1 ethyl acetate:acetonitrile) were combined and concentrated in vacuo to give 1.3 g of white foam. The fractions containing pure EtOCO-Phe(αMe)-Pro-Arg(Cbz)lactam (TLC R$_f$= 0.44, 4:1 ethyl acetate:acetonitrile) were combined and concentrated in vacuo to give 1.7 g of white foam. Fractions containing a mixture of the two diastereomers were combined and concentrated in vacuo to give 3.3 g of white foam. The mixture was chromatographed again and the pure fractions of each diastereomer were combined with those from the initial chromatography and concentrated in vacuo to give a total of 2.1 g (20%) of EtOCO-D-Phe(αMe)-Pro-Arg(Cbz)lactam and 3.7 g (35%) of EtOCO-Phe(αMe)-Pro-Arg(Cbz)lactam. The structure of the diastereomeric tripeptides was tentatively assigned by inference from the biological activity of the corresponding arginine aldehydes.
$^1$H NMR
FD-MS, m/e 621 (M$^+$)
Analysis Calculated for C$_{32}$H$_{40}$N$_6$O$_7$; C 61.92 H 6.50 N 13.54
Found C 61.74 H 6.51 N 13.33

H) EtOCO-D-Phe(αMe)-Pro-Arg-H·HCl

To a stirring solution of EtOCO-D-Phe(αMe)-Pro-Arg(Cbz)lactam (2 g, 3.2 mmol) in tetrahydrofuran (50 mL) at −23° C., was slowly added a solution of 1N LiAi(O-t-Bu)$_3$H (4.8 mL, 4.8 mmol) in tetrahydrofuran. After 2.5 h, the reaction mixture was poured into a stirring solution of cold 1N HCl (50 mL). The solution was then diluted with water (100 mL), washed with 1:1 tetrahydrofuran: hexanes (200 mL) and extracted twice with ethyl acetate and once with n-butanol. The combined ethyl acetate and n-butanol extracts were dried (Na$_2$SO$_4$), and concentrated in vacuo.

The residue was then dissolved in ethanol (75 mL) and then water (25 mL) and 1N HCl (10 mL) were added. To this stirring solution was then added 5% Pd on carbon (1 g). H$_2$ was then bubbled through the solution for 1.5 h, and then the reaction was flushed with N$_2$ and filtered over a pad of Celite®. The ethanol was removed in vacuo at 35° C. and then the residue was redissolved in water (25 mL). The pH of the aqueous solution was adjusted to 4.7 with Bio Rad ion exchange resin (basic form), filtered and lyophilized to give 1.15 g of a white powder. The product was then purified by RPHPLC (98/2 (A:B), 40 min; ramp up to 80/20 (A:B), 280 min; hold to 400 min) to give 0.49 g {29%} of pure EtOCO-D-Phe(αMe)-Pro-Arg-H·HCl dihydrate.
¹H NMR
FAB-MS, m/e 489 (MH⁺)
Analysis Calculated for $C_{24}H_{36}N_6O_5 \cdot HCl$; C 54.91 H 7.10 N 16.01 Cl 6.75
Found C 54.89 H 7.12 N 15.81 Cl 6.87

EXAMPLE 6

Preparation of N-Ethylsulfonyl-D-phenylalanyl(αmethyl)-L-prolinyl-L-arginine Aldehyde Hydrochloride

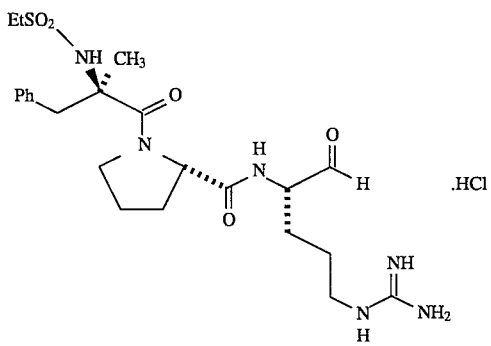

A) EtSO₂-D,L-Phe(αMe)-OH To a stirring suspension of D,L-Phe(αMe)-OH (9 g, 50 mmol) in tetrahydrofuran (250 mL) was added N,O-bis(trimethylsilyl)acetamide (15.3 g, 75 mmol). Upon clarification the solution was cooled to −78° C. and N,N-diisopropylethylamine (6.5 g, 50 mmol) was added, followed by ethanesulfonyl chloride (7.1 g, 55 mmol). The mixture was allowed to warm slowly to room temperature. After 16 h, water (100 mL) was added and then the organic solvent was removed in vacuo. The aqueous phase was diluted with 1N NaOH and washed twice with diethyl ether. The aqueous phase was then acidified to pH 3 with concentrated HCl and extracted three times with ethyl acetate. The combined ethyl acetate extracts were dried (Na₂SO₄), filtered and concentrated in vacuo to give 4.9 g (36%) of a white foam.
¹H NMR
FD-MS, m/e 271 (M⁺)
Analysis Calculated for $C_{12}H_{17}NO_4S$; C 53.12 H 6.32 N 5.16
Found: C 53.36 H 6.16 5.08
B) EtSO₂-D-Phe(αMe)-Pro-Arg-H·HCl By methods substantially equivalent to those described in Example 5-B, 5-C, 5-G, and 5-H, was prepared 1.1 g of EtSO₂-D-Phe(αMe)-Pro-Arg-H·HCl. The diastereomeric peptides were separated at the lactam stage (see Example 5-G) by silica gel chromatography (EtSO₂-D-Phe(αMe)-Pro-Arg(Cbz)lactam; TLC $R_f$=0.75, 4:1 ethyl acetate:acetonitrile). EtSO₂-D-Phe(αMe)-Pro-Arg-H·HCl was purified by RPHPLC (98/2 (A/B), 40 min; up to 80/20 (A/B), 280 min; hold to 400 min)
¹H NMR
FAB-MS, m/e 509 (MH⁺)
Analysis Calculated for $C_{23}H_{36}N_6O_5S \cdot HCl$; C 50.68 H 6.84 N 15.42
Found: C 50.59 H 6.67 15.35

EXAMPLE 7

Preparation Of N-Ethoxycarbonyl-phenylalanyl(αmethyl)-L-prolinyl-L-arginine Aldehyde Hydrochloride

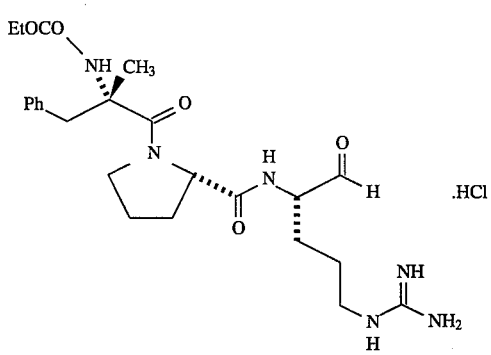

EtOCO-Phe(αMe)-Pro-Arg-H·HCl

By methods substantially equivalent to those described in Example 5-H, 0.78 g (42%) of EtOCO-Phe(αMe)-Pro-Arg-H·HCl was prepared from EtOCO-Phe((αMe)-Pro-Arg(Cbz)lactam (for preparation of EtOCO-Phe(αMe)-Pro-Arg(Cbz)lactam, see Example 5-G). EtOCO-PheαMe)-Pro-Arg-H·HCl hydrate was purified by RPHPLC (95/5 (A/B), 40 min; to 80/20 (A/B), 280 min; hold to 400 min)
¹H NMR
FAB-MS, m/e 489 (MH⁺)
Analysis Calc. for $C_{24}H_{36}N_6O_5 \cdot 1.1HCl \cdot 0.5H_2O$; C 53.61 H 7.14 N 15.63 Cl 7.25
Found: C 54.01 H 6.70 N 15.12 Cl 7.18

EXAMPLE 8

Preparation of N-(1-methylindolyl-2-carbonyl-D-phenylalanyl (αmethyl)-L-prolinyl-L-arginine Aldehyde Dihydrochloride

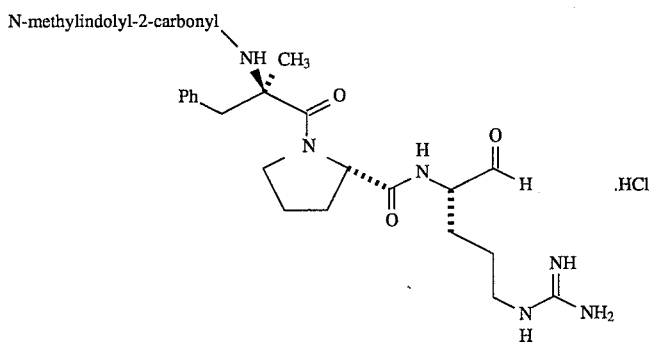

A) NMI-OPFF

To a solution of N-methyl indole-2-carboxylic acid (25 g, 143 mmol) and pentafluorophenol (35.3 g, 192 mmol) in tetrahydrofuran (250 mL) was added 1-(3-dimethylaminopropyl)-3-ethylcarbodiimide·HCl (30.5 g, 159 mmol). After stirring for 5 h, the solution was diluted with dichloromethane (200 mL) and hexanes (300 mL). The organic phase was washed with once with 1N NaHSO$_4$ (100 mL), three times with 1N K$_2$CO$_3$ (100 mL) and twice with brine. The organic phase was dried (Na$_2$SO$_4$), filtered and concentrated in vacuo to give a tan solid which was recrystalized from hexanes to give 38 g 78% yield) of an off white solid.
$^1$H NMR
FD-MS, m/e 341 (M$^+$)
Analysis Calculated for C$_{16}$H$_8$NO$_2$F$_5$; C 56.32 H 2.36 N 4.10
Found: C 56.53 H 2.37 4.20

B) NMI-D,L-Phe(αMe)-OH

To a stirring suspension of D,L-Phe(αMe)-OH (2.5 g, 14 mmol) in dimethylformamide (50 mL) was added N,O-bis(trimethylsilyl)acetamide (4.3 g, 21 mmol). Upon clarification of the solution, NMI-OPFF (5 g, 14.7 mmol) was added and the reaction was heated to 65° C. After 16 h, the heating mantle was removed and water (20 mL) was added. The solvents were then removed in vacuo and the residue was dissolved in 1N NaOH and washed three times with diethyl ether. The aqueous phase was then acidified to pH 3 with 5N HCl and extracted three times with ethyl acetate. The combined ethyl acetate extracts were dried (Na$_2$SO$_4$), filtered and concentrated in vacuo to give a yellow oil which was chromatographed over silica gel, eluting with 70% ethyl acetate:hexanes (0.5% acetic acid). The product containing fractions as judged by TLC were combined and concentrated in vacuo. The residue was dissolved in toluene and concentrated in vacuo three times (to remove acetic acid) to yield 4 g (85% yield) of a white solid.
$^1$H NMR
FD-MS, m/e 336 (M$^+$)
Analysis Calculated for C$_{20}$H$_{20}$N$_2$O$_3$; C 71.41 H 5.99 N 8.33
Found C 71.66 H 6.15 8.05

C) NMI-D-Phe(αMe)-Pro-Arg-H·HCl

By methods substantially equivalent to those described in Example 5-B, 5-C, 5-G, and 5-H, 1.4 g of NMI-D-Phe(αMe)-Pro-Arg-H·HCl was prepared. The diastereomeric peptides were separated at the lactam stage (see Example 5-G) by silica gel chromatography (NMI-D-Phe(αMe)-Pro-Arg(Cbz)lactam; TLC R$_f$=0.35, ethyl acetate). NMI-D-Phe(αMe)-Pro-Arg-H·HCl was purified by RPHPLC (95/5 (A/B) to 70/30 (A/B), 180 min; hold to 400 min).
$^1$H NMR
FAB-MS, m/e 574 (MH$^+$)
Analysis Calculated for C$_{31}$H$_{39}$N$_7$O$_4$·HCl; C 61.02 H 6.61 N 16.07 Cl 5.81
Found: C 61.30 H 6.40 15.98 Cl 6.09

EXAMPLE 9

Preparation Of 1-(Ethylsulfonylamino)cyclohexoyl-L-prolinyl-L-arginine Aldehyde Hydrochloride

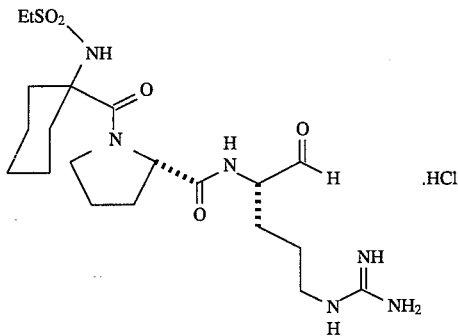

1-(ethylsulfonylamino)cyclohexoyl-Pro-Arg-H·HCl

By methods substantially equivalent to those described in Example 6, 0.95 g of 1-(ethylsulfonylamino)cyclohexoyl-pro-Arg-H·HCl hydrate was prepared from 1-amino-cyclohexane-1-carboxylic acid. 1-(ethylsulfonylamino)cyclohexoyl-pro-Arg-H·HCl hydrate was purified by RPHPLC (98/2 (A/B) to 80/20 (A/B), 240 min).
$^1$H NMR
FAB-MS, m/e 473 (MH$^+$)
Analysis Calc for C$_{20}$H$_{36}$N$_6$O$_5$·HCl·H$_2$O C 45.58 H 7.46 N 15.94 Cl 6.73
Found: C 45.49 H 7.37 N 15.65 Cl 6.54

EXAMPLE 10

Preparation of 1-(1-Methylindolyl-2-carbonylamino)cyclohexoyl-L-prolinyl-L-arginine Aldehyde Hydrochloride

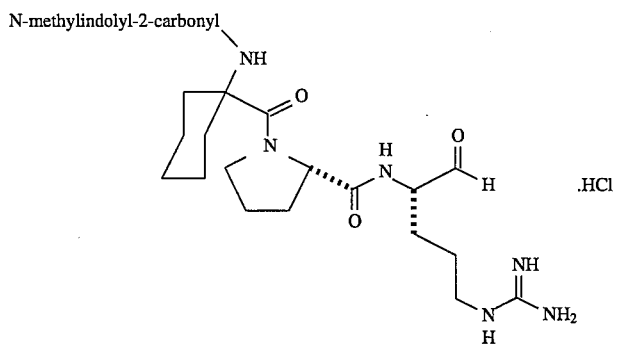

1-(N-methylindolyl-2-carbonylamino) cyclohexoyl-Pro-ArgH·HCl

By methods substantially equivalent to those described in Example 8, 1.9 g of 1-(N-methylindolyl-2-carbonylamino) cyclohexoyl-Pro-Arg-H·HCl hydrate was prepared from 1-amino-cyclohexane-1-carboxylic acid. Purification by RPHPLC was not required.

$^1$H NMR

FAB-MS, m/e 538 (MH$^+$)

Analysis Calculated for $C_{28}H_{39}N_7O_4 \cdot 2HCl \cdot 1.5H_2O$; C 52.75 H 6.96 N 15.38

Found: C 53.11 H 7.03 N 15.17

EXAMPLE 11

Preparation of N-Ethylsulfonylphenylalanyl(αmethyl)-L-prolinyl-L-arginine Aldehyde Hydrochloride

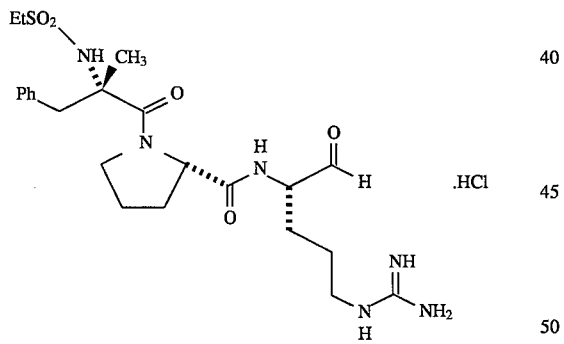

N-EtSO$_2$-Phe(αMe)-Pro-Arg-H·HCl

By methods substantially equivalent to those described in Example 6, 0.73 g of EtSO$_2$-Phe(αMe)-Pro-Arg-H·HCl dihydrate was prepared from EtSO$_2$-Phe(αMe)-Pro-Arg(Cbz)lactam (TLC R$_f$=0.66, 4:1 ethyl acetate:acetonitrile). EtSO$_2$-Phe(αMe)-Pro-Arg-H·HCl dihydrate was purified by RPHPLC (98/2 (A/B) to 85/15 (A/B), 180 min).

$^1$H NMR

FAB-MS, m/e 509 (MH$^+$)

Analysis Calc for $C_{23}H_{36}N_6O_5S \cdot HCl \cdot 2H_2O$; C 47.54 H 7.11 N 14.46 Cl 6.10

Found: C 47.80 H 6.65 N 14.23 Cl 6.67

EXAMPLE 12

Preparation of N-(1-methylindolyl-2-carbonyl)phenylalanyl (αmethyl)-L-prolinyl-L-arginine Aldehyde Hydrochloride

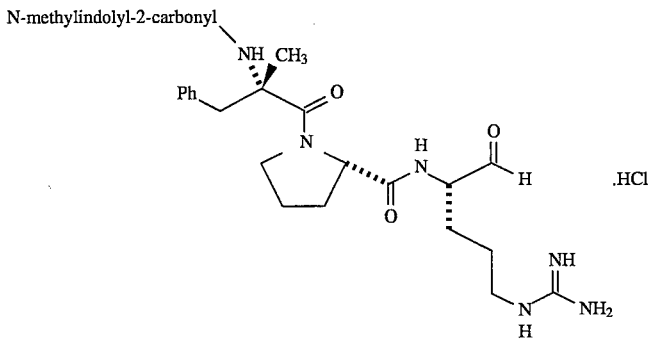

N-methylindolyl-2-carbonyl-Phe(αMe)-Pro-Arg-H·HCl

By methods substantially equivalent to those described in Example 8, 0.29 g of N-methylindolyl-2-carbonyl-Phe(αMe)-Pro-Arg-H·HCl hydrate was prepared from N-methylindolyl-2-carbonyl-Phe(αMe)-Pro-Arg(Cbz)lactam (TLC $R_f$=0.30, ethyl acetate). NMI-Phe(αMe)-Pro-Arg-H·HCl hydrate was purified by RPHPLC (95/5 (A/B) to 70/30 (A/B), 180 min; hold to 400 min).

$^1$H NMR

FAB-MS, m/e 574 (MH$^+$)

Analysis Calc for $C_{31}H_{39}N_7O_4 \cdot 1.1HCl \cdot 1.5H_2O$; C 58.10 H 6.78 N 15.30 Cl 6.09

Found: C 58.25 H 6.55 N 15.00 Cl 6.25

EXAMPLE 13

Preparation of N-Ethoxycarbonyl-L-phenylalanyl (αethyl)-L-prolinyl-L-arginine Aldehyde Hydrochloride

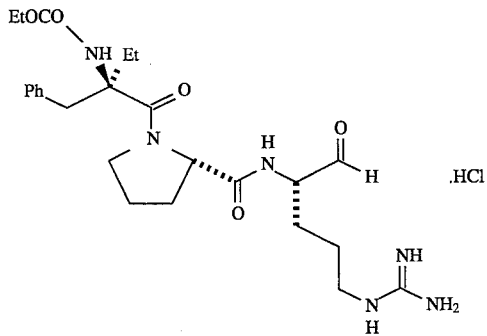

A) N-(diphenylmethylene)Phe-OMe

To a stirring suspension of Phe-OMe·HCl (89.3 g, 414 mmol) in dichloromethane (500 mL) was added a solution of benzophenone imine (75 g, 414 mmol) in dichloromethane (400 mL). After stirring for 16 h, the solution was filtered, washed with water, dried (Na$_2$SO$_4$) and concentrated in vacuo. The residue was recrystallized from diethyl ether to give 107 g (75% yield) of white solid.

$^1$H NMR

FD-MS, m/e 343 (M$^+$)

B) N-(diphenylmethylene)-Phe(αEt)-OMe

To a stirring solution of potassium t-butoxide (9 g, 80 mmol) in tetrahydrofuran (500 mL) at −78° C. was added a solution of N-(diphenylmethylene)Phe-OMe (25 g, 73 mmol) in tetrahydrofuran (250 mL). After 10 min, a solution of ethyl iodide (12.5 g, 80 mmol) in tetrahydrofuran (200 mL) was added. The cold bath was then removed and the solution was allowed to stir for 16 h. The solution was then filtered and the solvent was removed in vacuo. The residue was dissolved in diethyl ether and washed twice with water, once with brine, and then dried (Na$_2$SO$_4$), filtered and concentrated in vacuo. The residue was chromatographed over silica gel, eluting with a step gradient of 5% ethyl acetate:hexanes through 10% ethyl acetate:hexanes. The product containing fractions as judged by TLC were combined and concentrated in vacuo to yield 18.1 g (70% yield) of a thick yellow oil.

$^1$H NMR

FD-MS, m/e 371 (M$^+$)

C) D,L-Phe(αEt)-OMe

To a stirring solution of N-(diphenylmethylene)-Phe(αEt)-OMe (17.6 g, 47.4 mmol) in methanol (200 mL) was added 5N HCl (15 mL, 75 mmol). After 3 h, the solvent was removed in vacuo and the residue was dissolved in water and washed three times with diethyl ether. The aqueous phase was then adjusted to pH 10 with solid NaHCO$_3$ and extracted three times with ethyl acetate. The combined ethyl acetate extracts were then dried (Na$_2$SO$_4$), filtered and concentrated in vacuo to give 8.75 g (89% yield) of clear, colorless oil.

$^1$H NMR

FD-MS, m/e 208 (MH$^+$)

D) D,L-Phe(αEt)-OH

To a stirring solution of D,L-Phe(αEt)-OMe (24 g, 116 mmol) in tetrahydrofuran (200 mL) was added 5N NaOH (24 mL, 120 mmol), followed by water (50 mL) and methanol (50 mL) and the solution was heated to reflux. After 16 h, the solution was cooled to room temperature and the solvents were removed in vacuo. The residue was dissolved in water and washed three times with diethyl ether. The pH was adjusted to 6 with 5N HCl and the solution was concentrated to a volume of about 50 mL in vacuo. The precipitate was filtered, washed with water and dried to give 17.5 g (78% yield) of white solid.

$^1$H NMR

FD-MS, m/e 194 ( MH$^+$)

Analysis Calculated for $C_{11}H_{15}NO_2$; C 68.37 H 7.82 N 7.25

Found: C 68.58 H 7.65 N 7.41

E) EtOCO-D-Phe(αEt)-Pro-Arg-H·HCl

By methods substantially equivalent to those described in Example 5, 2.65 g of EtOCO-D-Phe(αEt)-Pro-Arg-H·HCl ethanolate was prepared from D,L-Phe(αEt)-OH. Purification of EtOCO-D-Phe(αEt)-Pro-Arg-H·HCl ethanolate by RPHPLC was not required. The diastereomeric peptides were separated at the dipeptide ester stage (see Example 5-B) by silica gel chromatography (EtOCO-D-Phe(αEt)-Pro-OBzl; TLC $R_f$=0.66, 50% ethyl acetate:hexanes).

¹H NMR
FAB-MS, m/e 503 ( MH⁺)
Analysis Calc for $C_{25}H_{38}N_6O_5 \cdot 1.1HCl \cdot 1.5EtOH$; C 55.20 H 7.50 N 14.85 Cl 6.89
Found: C 55.19 H 7.13 N 14.55 Cl 6.79

EXAMPLE 14

Preparation of N-Ethoxycarbonylphenylalanyl (αethyl)-L-prolinyl-L-arginine Aldehyde Hydrochloride

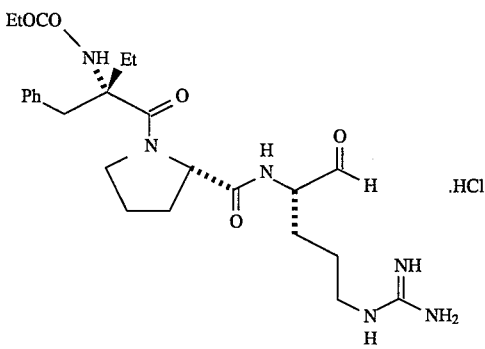

EtOCO-Phe(αEt)-Pro-Arg-H·HCl

By methods substantially equivalent to those described in Example 13, 2.15 g of EtOCO-Phe(αEt)-Pro-Arg-H·HCl ethanolate were prepared from EtOCO-Phe(αEt)-Pro-OBzl (TLC Rf=0.77, 50% ethyl acetate:hexanes). Purification of EtOCO-Phe(αEt)-Pro-Arg-H·HCl ethanolate by RPHPLC was not required.
¹H NMR
FAB-MS, m/e 503 (MH⁺)
Analysis Calculated for $C_{25}H_{38}N_6O_5 \cdot 2HCl \cdot 0.5EtOH$; C 52.17 H 7.24 N 14.04
Found: C 52.33 H 6.9 6 N 13.99

EXAMPLE 15

Preparation of N-Ethoxycarbonyl-D-phenylalanyl (αn-propyl)-L-prolinyl-L-arginine Aldehyde Hydrochloride

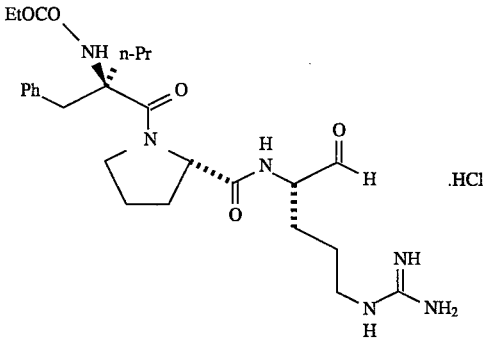

A) D,L-Phe(αn-Pr)-OMe

By methods substantially equivalent to those described in Example 13-A and 13-B, 10.1 g (63%) of D,L-Phe(αn-Pr)-OMe was prepared from N-(diphenylmethylene)-Phe-OMe and n-propyl iodide.
¹H NMR
FD-MS, m/e 222 (MH⁺)
B) EtOCO-D,L-Phe(αn-Pr)-OH To a stirring solution of D,L-Phe(αn-Pr)-OMe (9 g, 41 mmol) in tetrahydrofuran (250 mL) at 0° C. was added N,N-diisopropylethylamine (5.3 g, 41 mmol) followed by ethyl chloroformate (4.4 g, 41 mmol). After 3.5 h, the solvent was removed in vacuo and the residue was dissolved in ethyl acetate. The organic phase was washed twice with saturated aqueous NaHCO₃, once with brine, and then dried (Na₂SO₄), filtered and concentrated in vacuo.

The residue was dissolved in tetrahydrofuran (120 mL) and to this solution was added 5N NaOH (11 mL, 55 mmol) with vigorous stirring, followed by methanol (30 mL). The solution was heated to 55° C. and allowed to stir for 48 h. The solution was then cooled to room temperature and the solvents were removed in vacuo. The residue was dissolved in water and washed twice with diethyl ether. The aqueous phase was adjusted to pH 3 with conc. HCl and extracted twice with ethyl acetate. The combined ethyl acetate extracts were dried (Na₂SO₄), filtered and concentrated in vacuo to yield 10.3 g (91%) of a yellow solid.
¹H NMR
FD-MS, m/e 279 (M⁺)
C) EtOCO-D-Phe(αn-Pr)-Pro-Arg-H·HCl By methods substantially equivalent to those described in Example 5-B, 5-C, 5-G and 5-H, 0.69 g of EtOCO-D-Phe(αn-Pr)-Pro-Arg-H·HCl was prepared. The diastereomeric peptides were separated at the dipeptide ester stage (see Example 5-B) by silica gel chromatography (EtOCO-D-Phe(αn-Pr)-Pro-OBzl; TLC Rf=0.77, 50% ethyl acetate:hexanes). EtOCO-D-Phe(αn-Pr)-Pro-Arg-H·HCl was purified by RPHPLC (98/2 (A/B), 60 min; to 80/20 (A/B), 300 min).
¹H NMR
FAB-MS, m/e 517 (MH⁺)
Analysis Calculated for $C_{26}H_{40}N_6O_5 \cdot HCl$; C 56.46 H 7.47 N 15.19
Found: C 56.22 H 7.41 N 15.11

EXAMPLE 16

Preparation of N-Ethoxycarbonylphenylalanyl(αn-propyl)-L-prolinyl-L-arginine Aldehyde Hydrochloride

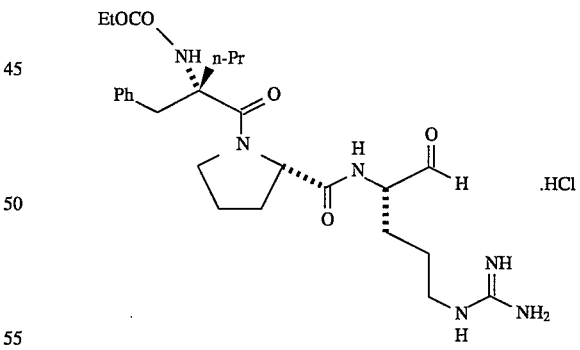

EtOCO-Phe(αn-Pr)-Pro-Arg-H·HCl

By methods substantially equivalent to those described in Example 15, 0.34 g of EtOCO-Phe(αn-Pr)-Pro-Arg-H·HCl was prepared from EtOCO-Phe(αn-Pr)-Pro-OBzl (TLC R_f=0.67, 50% ethyl acetate:hexanes). EtOCO-Phe(αn-Pr)-Pro-Arg-H·HCl was purified by RPHPLC (98/2 (A/B), 60 min; to 80/20 (A/B), 300 min).
¹H NMR
FAB-MS, m/e 517 (MH⁺)
Analysis Calculated for $C_{26}H_{40}N_6O_5 \cdot HCl$; C 56.46 H 7.47 N 15.19

Found: C 56.75 H 7.55 N 15.47

EXAMPLE 17

Preparation of N-Ethoxycarbonyl-D-phenylalanyl (αn-butyl)-L-prolinyl-L-arginine Aldehyde Hydrochloride

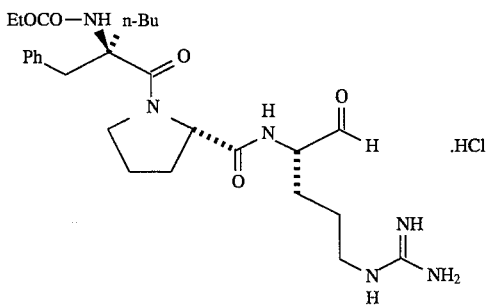

EtOCO-D-Phe(αn-Bu)-Pro-Arg-H·HCl

By methods substantially equivalent to those described in Example 15, 2.2 g of EtOCO-D-Phe(αn-Bu)-Pro-Arg-H·HCl was prepared, starting with N-(diphenylmethylene)-Phe-OMe and n-butyl iodide. The diastereomeric peptides were separated at the dipeptide ester stage (see Example 5-B) by silica gel chromatography (EtOCO-D-Phe(αn-Bu)-Pro-OBzl; TLC Rf=0.86, 50% ethyl acetate:hexanes). EtOCO-D-Phe(αn-Bu)-Pro-Arg-H·HCl was purified by RPHPLC (98/2 (A/B), 60 min; to 85/15 (A/B), 300 min).
$^1$H NMR
FAB-MS, m/e 531 (MH$^+$)
Analysis Calculated for $C_{27}H_{42}N_6O_5$·HCl; C 57.18 H 7.64 N 14.82
Found: C 57.32 H 7.74 N 14.95

EXAMPLE 18

Preparation of N-Ethoxycarbonylphenylalanyl (αn-butyl)-L-prolinyl-L-arginine Aldehyde

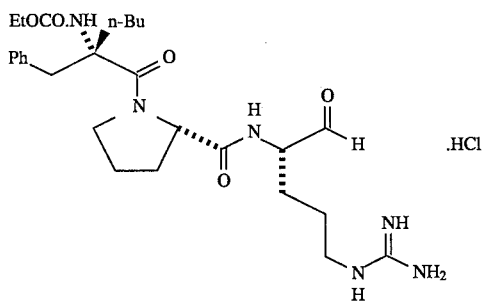

EtOCO-Phe(αn-Bu)-Pro-Arg-H·HCl

By methods substantially equivalent to those described in Example 17, 1.47 g of EtOCO-Phe(αn-Bu)-Pro-Arg-H·HCl was prepared from EtOCO-Phe(αn-Bu)-Pro-OBzl (TLC R$_f$=0.74, 50% ethyl acetate:hexanes). EtOCO-Phe(αn-Bu)-Pro-Arg-H·HCl was purified by RPHPLC (98/2 (A/B), 60 min; to 85/15 (A/B), 300 min).
$^1$H NMR
FAB-MS, m/e 531 (MH$^+$)
Analysis Calculated for $C_{27}H_{42}N_6O_5$·HCl; C 57.18 H 7.64 N 14.82
Found: C 56.92 H 7.59 N 14.76

EXAMPLE 19

Preparation of N-Ethylsulfonyl-(D,L)-phenylglycinyl(αmethyl)-L-prolinyl-L-arginine Aldehyde Hydrochloride

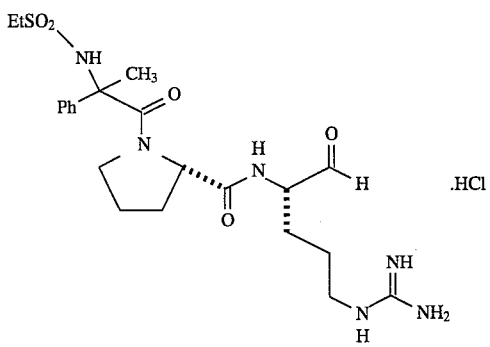

EtSO$_2$-D,L-Phg(αMe)-Pro-Arg-H·HCl

By methods substantially equivalent to those described in Example 15, 0.21 g of EtSO$_2$-D,L-Phg(αMe)-Pro-Arg-H·HCl hydrate was prepared starting from D,L-Phg-OMe·HCl and using EtSO$_2$Cl in place of EtOCOCl, and CH$_3$I in place of n-propyliodide. EtSO$_2$-D,L-Phg(αMe)-Pro-Arg-H·HCl hydrate was purified by RPHPLC (98/2 (A/B), 30 min; to 80/20 (A/B), 240 min). The diastereomers could not be separated during the course of this synthesis and thus, the product was prepared and tested as a mixture of isomers.
$^1$H NMR
FAB-MS, m/e 495 (MH$^+$)
Analysis Calculated for $C_{22}H_{34}N_6O_5S$·1.2HCl·H$_2$O; C 47.49 H 6.74 N 15.10
Found: C 47.50 H 6.44 N 14.91

EXAMPLE 20

Preparation of N-Ethoxycarbonylglycinyl(α,αdi-n-butyl)-L-prolinyl-L-arginine Aldehyde Hydrochloride

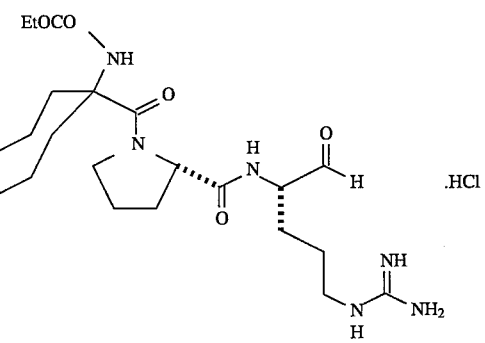

EtOCO-Gly(α,αdi-n-Bu)-Pro-Arg-H·HCl

By methods substantially equivalent to those described in Example 15, 1.4 g of EtOCO-Gly(α,αdi-n-Bu)-Pro-Arg-H·HCl hydrate was prepared starting with N-(diphenylmethylene)Gly-OEt and two equivalents of n-butyl iodide. Reduction of the intermediate EtOCO-Gly(α,αdi-n-Bu)-Pro-Arg(Cbz)lactam was accomplished by a method similar to that described in Example 5-G, except lithium aluminum hydride was used as the reducing agent at −78° C. EtOCO-Gly(α,αdi-n-Bu)-Pro-Arg-H·HCl hydrate was purified by RPHPLC (98/2 (A/B), 60 min; to 80/20 (A/B), 320 min).

$^1$H NMR
FAB-MS, m/e 497 (MH$^+$)
Analysis Calc for $C_{24}H_{44}N_6O_5 \cdot 1.2HCl \cdot H_2O$; C 51.62 H 8.52 N 15.05 Cl 7.62
Found: C 51.82 H 7.91 N 14.69 Cl 7.75

EXAMPLE 21

Preparation of N-Methylsulfonyl-D-phenylalanyl(αmethyl)-L-prolinyl-L-arginine Aldehyde Hydrochloride

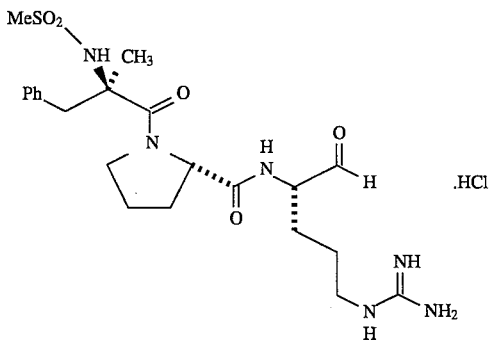

MeSO$_2$-D-Phe(αMe)-Pro-Arg-H·HCl

By methods substantially equivalent to those described in Example 6, 0.16 g of MeSO$_2$-D-Phe(αMe)-Pro-Arg-H·HCl hydrate was prepared, using MeSO$_2$Cl in place of EtSO$_2$Cl. The diastereomeric peptides were separated at the tripeptide arginine aldehyde stage by RPHPLC (98/2 (A/B), 80 min; up to 85/15 (A/B), 320 min). Stereochemistry is tentatively assigned based on the thrombin inhibitory activity of Example 21 and Example 22.
$^1$H NMR
FAB-MS, m/e 495 (MH$^+$)
Analysis Calc for $C_{22}H_{34}N_6O_5S \cdot 1.1HCl \cdot H_2O$; C 47.81 H 6.77 N 15.20 Cl 7.06
Found: C 47.73 H 6.45 N 15.25 Cl 7.12

EXAMPLE 22

Preparation of N-Methylsulfonylphenylalanyl (αmethyl)-L-prolinyl-L-arginine Aldehyde Hydrochloride

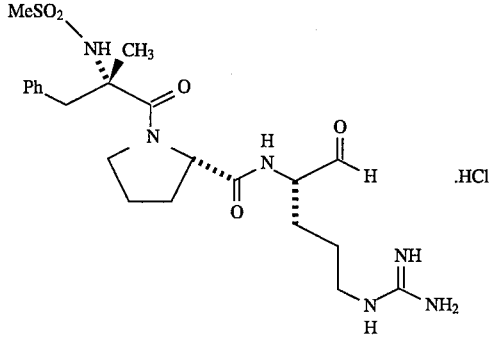

MeSO$_2$-Phe(αMe)-Pro-Arg-H·HCl

By methods substantially equivalent to those described in Example 6, 0.16 g of MeSO$_2$-Phe(αMe)-Pro-Arg-H·HCl hydrate was prepared, using MeSO$_2$Cl in place of EtSO$_2$Cl. The diastereomeric peptides were separated at the tripeptide arginine aldehyde stage by RPHPLC (98/2 (A/B), 80 min; up to 85/15 (A/B), 320 min). Stereochemistry is tentatively assigned based on the thrombin inhibitory activity of Example 21 and Example 22.
$^1$H NMR
FAB-MS, m/e 495 (MH$^+$)
Analysis Calc for $C_{22}H_{34}N_6O_5S \cdot 1.1HCl \cdot H_2O$; C 47.81 H 6.77 N 15.20 Cl 7.06
Found C 47.81 H 6.38 N 14.96 Cl 7.06

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis. Further, the compounds of the present invention are believed to be orally active.

The invention in one of its aspects provides a method of inhibiting thrombin in mammals comprising administering to a mammal in need of treatment an effective (thrombin inhibiting) dose of a compound of formula I.

In another of its aspects, the invention provides a method of treating a thromboembolic disorder comprising administering to a mammal in need of treatment an effective (thromboembolic disorder therapeutic and/or prophylaetic amount) dose of a compound of formula I.

The invention in another of its aspects provides a method of inhibiting coagulation in mammals comprising administering to mammal in need of treatment an effective (coagulation inhibiting) dose of a compound of formula I.

The thrombin inhibition, coagulation inhibition, and thromboembolic disorder treatment, contemplated by the present method includes both medical therapeutic and/or prophylactic treatment as appropriate.

In a further embodiment the invention relates to treatment, in a human or animal, of conditions where inhibition of thrombin is required. The compounds of the invention are expected to be useful in animals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in prophylaxis of atherosclerotic diseases such as coronary arterial disease, cerebral arterial disease and peripheral arterial disease. Further, the compounds are expected to be useful together with thrombolytics in myocardial infarction. Further, the compounds have expected utility in the treatment or prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vivo. Still further, the compounds have expected utility in other diseases and disorders where blood coagulation could be a fundamental contributing process or a source of secondary pathology, such as cancer, including metastasis, inflammatory diseases, including arthritis and diabetes. The anti-coagulant compound is administered orally or parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (tPA), modified tPA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical formulations for use in the above described therapeutic method. Pharmaceutical formulations of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9%), 5% dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 ml sterile glass ampoule. Another example of a unit dosage formulation comprises about 10 mg of a compound of the present invention as a pharmaceutically acceptable salt in 20 ml of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical formulation comprising an effective amount of a compound of Formula I or a pharmaceutically acceptable salt or solvate thereof in association with a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. The compositions of this invention may be formulated so as to provide quick, sustained, or delayed release of the active ingredient after administration to the patient by employing procedures well know in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

FORMULATION 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

FORMULATION 2

A tablet is prepared using the ingredients below:

|  | Quantity (mg/capsule) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

FORMULATION 3

An aerosol solution is prepared containing the following components:

|                                       | Weight |
|---------------------------------------|--------|
| Active ingredient                     | 0.25   |
| Ethanol                               | 25.75  |
| Propellant 22 (Chlorodifluoromethane) | 70.00  |
| Total                                 | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of active ingredient, are made as follows:

| Active ingredient                              | 60 mg  |
|------------------------------------------------|--------|
| Starch                                         | 45 mg  |
| Microcrystalline cellulose                     | 35 mg  |
| Polyvinylpyrrolidone (as 10% solution in water)| 4 mg   |
| Sodium carboxymethyl starch                    | 4.5 mg |
| Magnesium stearate                             | 0.5 mg |
| Talc                                           | 1 mg   |
| Total                                          | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of active ingredient, are made as follows:

| Active ingredient          | 80 mg  |
|----------------------------|--------|
| Starch                     | 59 mg  |
| Microcrystalline cellulose | 59 mg  |
| Magnesium stearate         | 2 mg   |
| Total                      | 200 mg |

The active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of active ingredient, are made as follows:

| Active ingredient                | 225 mg    |
|----------------------------------|-----------|
| Saturated fatty acid glycerides  | 2,000 mg  |
| Total                            | 2,225 mg  |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of active ingredient per 5 ml dose, are made as follows:

| Active ingredient             | 50 mg   |
|-------------------------------|---------|
| Sodium carboxymethyl cellulose| 50 mg   |
| Syrup                         | 1.25 ml |
| Benzoic acid solution         | 0.10 ml |
| Flavor                        | q.v.    |
| Color                         | q.v.    |
| Purified water to total       | 5 ml    |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg   |
|-------------------|----------|
| Isotonic saline   | 1,000 ml |

The solution of the above ingredients generally is administered intravenously to a subject at a rate of 1 ml per minute.

The compounds provided by the invention (formula I) selectively inhibit the action of thrombin in mammals.

The ability of the compounds of the present invention to be an effective and orally active thrombin inhibitor is evaluated in one or more of the following assays.

The inhibition of thrombin is demonstrated by in vivo inhibition of the amidase activity of thrombin as measured in an assay in which thrombin hydrolyzes the chromogenic substrate, N-benzoylphenylalanyl-L-valyl-L-arginyl-p-nitroanilide, N-benzoyl-Phe-L-Val-L-Arg-p-nitroanilide.

The assay is carried out by mixing 50 µl buffer (0.03M Tris, 0.15M NaCl, pH 7.4), 25 µl of human thrombin solution (purified human thrombin, Enzyme Research Laboratories, South Bend, Ind., at 8 NIH units/ml) and 25 µl of test compound in a solvent (in 50% aqueous methanol, v:v). Then 150 µl of an aqueous solution of the chromogenic substrate (at 0.25 mg/ml) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to free thrombin values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$\text{Thrombin} + I \leftrightarrows \text{Thrombin} - I$$

$$\text{Kass} = \frac{[\text{Thrombin } I]}{[(\text{Thrombin}) \times (I)]}$$

Kass is calculated for a range of concentrations of test compounds and the mean value is reported in units of liter per mole.

By substantially following the procedures described above for human thrombin, and using other human blood coagulation system serine proteases, and using fibrinolytic system serine proteases, with the appropriate chromogenic substrates, identified below, selectivity of the compounds of the present invention with respect to the coagulation factor serine proteases and to the fibrinolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952 incorporated by reference herein in its entirety. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from KabiVitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.; nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Table 1 which follows lists the Kass value obtained with the indicated compound represented by the formula 1.

TABLE 1

| Example No. | Kass (L/mol × 10⁶) | | | | |
|---|---|---|---|---|---|
| | Human Thrombin | Xa | Trypsin | Plasmin | t-PA |
| 1 | 79. | 0.06 | 29. | 0.55 | 0.02 |
| 2 | 12. | 0.13 | 14. | 0.31 | 0.0034 |
| 3 | 350. | 0.27 | 43. | 0.77 | 0.0045 |
| 4 | 75. | 0.12 | 17. | 0.17 | 0.0028 |
| 5 | 75. | 0.044 | 2.4 | 0.059 | 0.00079 |
| 6 | 24. | 0.11 | 20. | 0.31 | 0.051 |
| 7 | 5.0 | 0.025 | 1.7 | 0.020 | 0.00072 |
| 8 | 25. | 0.013 | 1.3 | 0.0083 | 0.0022 |
| 9 | 3.2 | 0.036 | 0.42 | 0.010 | 0.00034 |
| 10 | 5.7 | 0.024 | 0.45 | 0.0071 | 0.0011 |
| 11 | 0.6 | 0.027 | 1.7 | 0.056 | 0.007 |
| 12 | 2.8 | 0.002 | 0.18 | 0.001 | 0.009 |
| 13 | 57. | 0.036 | 4.9 | 0.12 | 0.002 |
| 14 | 6.5 | 0.078 | 4.7 | 0.058 | 0.001 |
| 15 | 47. | 0.030 | 4.9 | 0.12 | <0.001 |
| 16 | 38. | 0.077 | 7.3 | 0.074 | <0.001 |
| 17 | 66. | 0.095 | 21. | 0.066 | <0.001 |
| 18 | 47. | 0.088 | 15. | 0.13 | 0.001 |
| 19 | 430. | 0.49 | 42. | 1.2 | 0.023 |
| 20 | 24. | 0.22 | 38. | 0.24 | 0.010 |
| 21 | 31. | 0.23 | 28. | 0.56 | 0.027 |
| 22 | 2.1 | 0.033 | 1.4 | 0.031 | 0.0023 |

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysiss-paring (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 ul thrombin (73 NIH unit/ml) to 100 ul human plasma which contained 0.0229 uCi 125-iodine labeled fibrinogen. Clot lysis is studied by overlaying the clots with 50 ul of urokinase or streptokinase (50, 100, or 1000 unit/ml) and incubating for 20 hours at room temperature. After incubation the tubes are centrifuged in a Beckman Microfuge. 25 ul of supernate is added into 1.0 ml volume of 0.03 M tris/0.15M NaCl buffer for gamma counting.

Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/ml concentrations. Rough approximations of IC50 values are estimated by linear extrapolations from data points to a value which would represent 50 percent of lysis for that particular concentration of fibrinolytic agent.

Anticoagulant Activity Materials

Dog plasma and rat plasma are obtained from conscious mixed-breed hounds (either sex, hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Blochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Ann Arbor, Mich.) is used for coagulation assays in plasma.

Methods Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 ml saline and 0.05 ml Thromboplastin-C reagent to 0.05 ml test plasma. The activated partial thromboplastin time (APTT) is measured by incubation of 0.05 ml test plasma with 0.05 ml Actin reagent for 120 seconds followed by 0.05 ml CaCl2 (0.02M). The thrombin time (TT) is measured by adding 0.05 ml saline and 0.05 ml thrombin (10 NIH units/ml) to 0.05 ml test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

TABLE 2

| Example No. | Human Plasma Anticoagulation 2 × Clotting time (ng/mL) | | |
|---|---|---|---|
| | TT | APTT | PT |
| 1 | 59 | 1,800 | 1,980 |
| 2 | 160 | 2,100 | 3,600 |
| 3 | 28 | 960 | 1,400 |
| 4 | 42 | 1,400 | 1,100 |
| 5 | 48 | 2,500 | 2,200 |
| 6 | 100 | 1,600 | 2,400 |
| 7 | 190 | 5,400 | 6,100 |
| 8 | 220 | 2,800 | 4,200 |
| 9 | 300 | 12,000 | 11,000 |
| 10 | 1,000 | 11,000 | 9,200 |
| 11 | 300 | 5,400 | 7,300 |
| 12 | 1,800 | 21,000 | 37,000 |
| 13 | 93 | 3,200 | 3,300 |
| 14 | 310 | 5,000 | 7,100 |
| 15 | 71 | 4,100 | 2,800 |
| 16 | 98 | 2,700 | 2,200 |
| 17 | 160 | 3,400 | 3,000 |

TABLE 2-continued

| Example No. | Human Plasma Anticoagulation 2 × Clotting time (ng/mL) | | |
|---|---|---|---|
| | TT | APTT | PT |
| 18 | 91 | 3,100 | 2,400 |
| 19 | 52 | 1,200 | 2,100 |
| 20 | 120 | 3,000 | 2,800 |
| 21 | 41 | 1,500 | 1,600 |
| 22 | 560 | 12,000 | 11,000 |

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

FeCl$_3$ Model Of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. FeCl$_3$ hexahydrate is dissolved in water and the concentration (20%) is expressed in terms of the actual weight of FeCl$_3$ only. To injure the artery and induce thrombosis, 2.85 ul is piperted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269,1990).

Spontaneous Thrombolysis Model

In vitro data suggests that peptide thrombin inhibitors inhibit thrombin and at higher concentrations may inhibit other serine proteases, such as plasmin and tissue plasminogen activator. To assess if the compounds inhibited fibrinolysis in vivo, the rate of spontaneous thrombolysis is determined by implanting a labeled whole blood clot into the pulmonary circulation. Rat blood (1 ml) is mixed rapidly with bovine thrombin (4 IU, Parke Davis) and $^{125}$I human fibrogen (5 μCi, ICN), immediately drawn into silastic tubing and incubated at 37° C. for 1 hr. The aged thrombus is expelled from the tubing, cut into 1 cm segments, washed 3× in normal saline and each segment is counted in a gamma counter. A segment with known counts is aspirated into a catheter that is subsequently implanted into the jugular vein.

The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{\text{(injected cpm} - \text{lung cpm)}}{\text{injected cpm}} \times 100$$

The fibrinolytic dissolution of the implanted clot occurs time-dependently (see J. P. Clozel, *Cardiovas. Pharmacol.*, 12:520, 1988).

Coagualation Parameters

Plasma thrombin time (TT) and activated partial thromboplastin time (APTT) are measured with a fibrometer. Blood is sampled from a jugular catheter and collected in syringe containing sodium citrate (3.8%, 1 part to 9 parts blood). To measure TT, rat plasma (0.1 ml) is mixed with saline (0.1 ml) and bovine thrombin (0.1 ml, 30 U/ml in TRIS buffer; Parke Davis) at 37° C. For APTT, plasma (0.1 ml) and APTT solution (0.1 ml, Organon Teknika) are incubated for 5 minutes (37° C.) and $CaCl_2$ (0.1 ml 0.025M) is added to start coagulation. Assays are done in duplicate and averaged.

Index of Bioavailability

A measure of bioactivity, plasma thrombin time (TT), serves as a substitute for the assay of parent compound on the assumption that increments in TT result from thrombin inhibition by parent only. The time course of the effect of the thrombin inhibitor upon TT is determined after i.v. bolus administration to anesthetized rats and after oral treatment of fasted conscious rats. Due to limitations of blood volume and the number of points required to determine the time course from time of treatment to the time when the response returned to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC \text{ po}}{AUC \text{ iv}} \times \frac{\text{Dose iv}}{\text{Dose po}} \times 100$$

Compounds

Compound solutions are prepared fresh daily in normal saline and are injected as a bolus or are infused starting 15 min before and continuing throughout the experimental perturbation which is 15 minutes in the arteriovenuous shunt model and 60 minutes in the $FeCl_3$ model of arterial injury and in the spontaneous thrombolysis model. Bolus injection volume is 1 ml/kg for i.v., and 5 ml/kg for p.o. and infusion volume is 3 ml/hr.

Statistics

Results are expressed as means +/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50% relative humidity; and lighted from 0600–1800 hours.

Pharmacokinetic Model

Test compound is formulated immediately prior to dosing by dissolving in sterile 0.9% saline to a 5 mg/ml preparation. Dogs are given a single 2 mg/kg dose of test compound by oral gavage. Blood samples (4.5 ml) are taken from the cephalic vein at 0.25, 0.5, 0.75, 1,2,3,4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to $pH_7$ with phosphoric acid (60:40, v/v). Plasma concentration of test compound is recorded and used to calculate the pharmacokinetic parameters: elimination rate constant, Ke; total clearance, Clt; volume of distribution, VD; time of maximum plasma test compound concentration, Tmax; maximum concentration of test compound at Tmax, Cmax; plasma half-life, to.5; area under the curve, A.U.C.; and fraction of test compound absorbed, F.

Canine Model of Coronary Artery Thrombosis

Surgical preparation and instrumentation of the dogs are as described in Jackson, et al., *Circulation*, 92, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50% inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration ReGimens

Electrolytic injury of the intima of the LCX is produced by applying 100-µA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 h. A 2-h infusion of the compounds of the present invention at doses of 0.5 and 1 mg/kg/h is begun simultaneously with an infusion of thrombotic agent (e.g. tissue plasminogen activator, streptokinase, APSAC). Reperfusion is followed for 3 h after administration of test compound. Reocclusion of coronary arteries after successful thrombolysis is defined as zero CBF which persisted for $\geq$ 30 min.

Hematology and Template Bleeding Time Determinations

Whole blood cell counts, hemoglobin, and hematocrit values are determined on a 40-µl sample of citrated (3.8%) blood (1 part citrate:9 parts blood) with a hematology analyzer (Cell-Dyn 900, Sequoia-Turner. Mount View, Calif., U.S.A.). Gingival template bleeding times are determined with a Simplate II bleding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, 21, 587–599 (1993).

We claim:

1. A compound having the formula

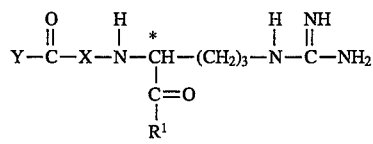

where $R^1$ is hydrogen;

X is prolinyl or azetidinyl-2-carbonyl;

Y is a group

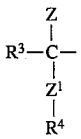

where Z is hydroxy, $C_1$–$C_4$ alkoxy or —$NHR^2$;

$R^2$ is hydrogen, $C_1$–$C_6$ alkyl, cyclopentyl, cyclohexyl, a group

or —$S(O)_n$—$R^5$ where $R^5$ is $C_1$–$C_4$ alkyl, $C_1$–$C_2$ perfluoroalkyl, $C_1$–$C_4$ alkoxy, ($C_1$–$C_4$ alkoxy)$C_1$–$C_4$ alkyl, cyclopentyl, cyclohexyl, amino, mono ($C_1$–$C_4$)alkylamino, di($C_1$–$C_4$)alkylamino, unsubstituted or substituted aryl, where aryl is phenyl or naphthyl, a 5 or 6 member unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

n is 1 or 2;

$R^3$ is $C_1$–$C_4$ alkyl, unsubstituted or substituted phenyl or unsubstituted or substituted benzyl;

$Z^1$ is a bond or —$CH_2$—;

$R^4$ is $C_1$–$C_6$ alkyl, $C_1$–$C_4$ alkoxy, cyclopentyl, cyclohexyl, unsubstituted or substituted aryl where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted bicyclic heterocyclic group having one or two heteroatoms which are the same or different and which are selected from sulfur, oxygen and nitrogen;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted hydrocarbyl group; and pharmaceutically acceptable salts and solyates thereof;

provided that when (a-i) $R^3$ is methyl or ethyl; $Z^1$ is a bond; $R^4$ is cyclopentyl, cyclohexyl, unsubstituted or substituted aryl where aryl is phenyl or naphthyl or $R^4$ is thienyl or furyl; and x is prolinyl or azetidinyl-2-carbonyl; or (a-ii) $R^4$—$Z^1$— taken together form methyl or ethyl; $R^3$ is unsubstituted or substituted phenyl; and X is prolinyl or azetidinyl-2-carbonyl; or when (b-i) $R^3$ is methyl or ethyl; $Z^1$ is —($CH_2$)—; $R^4$ is unsubstituted or substituted phenyl; and X is azetidinyl-2-carbonyl; or (b-ii) $R^4$—$Z^1$— taken together form methyl or ethyl; $R^3$ is unsubstituted or substituted benzyl; and x is azetidinyl-2-carbonyl; or further when (c) $R^3$ and $R^4$ are taken together to afford a cyclopentyl or cyclohexyl; and X is prolinyl;

then Z is not hydroxy, $C_1$-$C_4$ alkoxy or $NHR^2$ in which $R^2$ is hydrogen, $C_1$-$C_6$ alkyl or a group

in which $R^5$ is $C_1$-$C_4$ alkyl, $C_1$-$C_2$ perfluoroalkyl or $C_1$-$C_4$ alkoxy.

2. A compound of claim 1 where $R^1$ is hydrogen;

Z is —$NHR^2$, where $R^2$ is

or —$S(O)_n$—$R^5$;

$R^3$ is $C_1$-$C_4$ alkyl;

$R^4$ is unsubstituted or substituted aryl where aryl is phenyl or naphthyl;

$R^5$ is $C_1$-$C_4$ alkyl, $C_1$-$C_4$ alkoxy, a 5 or 6 membered unsubstituted or substituted heterocyclic ring having one or two nitrogen atoms, or a 9 or 10 membered unsubstituted or substituted fused bicyclic heterocyclic group having one or two nitrogen atoms;

n is 1 or 2; or

Z is taken together with $R^3$ to afford an azetidinyl group, a 5 or 6 membered unsubstituted or substituted heterocyclic ring having one or two nitrogen atoms or a 9 or 10 membered unsubstituted or substituted fused bicyclic heterocyclic group having one or two nitrogen atoms; and pharmaceutically acceptable salts and solvates thereof.

3. A compound of claim 2 where $R^1$ is hydrogen;

X is prolinyl or azetidinyl-2-carbonyl;

Y is a group

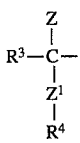

where $R^3$ is $C_1$-$C_4$ alkyl;

$Z^1$ is a bond or $CH_2$—;

$R^4$ is unsubstituted or monosubstituted phenyl; and

Z is —$NHR^2$, where $R^2$ is

in which $R^5$ is a 9 or 10 membered unsubstituted or monosubstituted fused bicyclic heterocyclic group having one nitrogen atom; or $R^2$ is a group —$SO_2R^5$ in which $R^5$ is $C_1$-$C_4$ alkyl; or $R^3$ and Z are taken together to afford an azetidinyl group, or a 5 or 6 membered unsubstituted heterocyclic ring having one or two nitrogen atoms; and pharmaceutically acceptable salts and solvates thereof.

4. A compound of claim 2 or claim 3 where $R^1$ is hydrogen;

Z is —$NHR^2$, where $R^2$ i

$R^3$ is $C_1$-$C_4$ alkyl;

$Z^1$ is —$CH_2$—;

$R^4$ is unsubstituted or monosubstituted phenyl;

$R^5$ is $C_1$-$C_4$ alkoxy, or a 9 or 10 membered unsubstituted or monosubstituted fused bicyclic heterocyclic group having one nitrogen atom; and pharmaceutically acceptable salts and solvates thereof.

5. A compound of claim 3 where $R^1$ is hydrogen;

Z is —$NHR^2$, where $R^2$ is —$SO_2R^5$;

$R^3$ is $C_1$-$C_4$ alkyl $R^4$ is unsubstituted or monosubstituted phenyl;

$R^5$ is $C_1$-$C_4$ alkyl; and pharmaceutically acceptable salts and solvates thereof.

6. A compound of claim 3 where $R^1$ is hydrogen;

Z is —$NHR^2$;

$R^4$ is unsubstituted or monosubstituted phenyl; and $R^3$ and Z are taken together to afford an azetidinyl group, or a 5 or 6 membered unsubstituted heterocyclic ring having one or two nitrogen atoms; and pharmaceutically acceptable salts and solvates thereof.

7. A compound of claim 3 which is 1-methylindolyl-2-carbonyl-D-(αmethyl)phenylglycine-L-azetidinyl-2-carbonyl-L-arginine aldehyde and pharmaceutically acceptable salts and solvates thereof.

8. A compound of claim 3 which is N-ethoxycarbonyl-D-phenylalanyl(αmethyl)-L-prolinyl-L-arginine aldehyde and pharmaceutically acceptable salts and solvates thereof.

9. A compound of claim 5 which is N-ethylsulfonyl-(D,L)-phenylglycinyl(αmethyl)-L-prolinyl-L-arginine aldehyde and pharmaceutically acceptable salts and solvates thereof.

10. A compound of claim 6 which is prolinyl(αbenzyl)-L-prolinyl-L-arginine aldehyde and pharmaceutically acceptable salts and solvates thereof.

11. A compound of claim 6 which is azetidinyl(αbenzyl)-L-prolinyl-L-arginine aldehyde and pharmaceutically acceptable salts and solvates thereof.

12. A pharmaceutical formulation comprising in association with a pharmaceutically acceptable carrier, diluent, or excipient, a compound of the formula

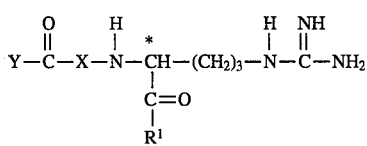   I where
- $R^1$ is hydrogen;
- X is prolinyl or azetidinyl-2-carbonyl;
- Y is a group

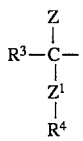

where Z is hydroxy, $C_1$-$C_4$ alkoxy or —$NHR^2$;
$R^2$ is hydrogen, $C_1$-$C_6$ alkyl, cyclopentyl, cyclohexyl, a grou

or —$S(O)_nR^5$
where $R^5$ is $C_1$-$C_4$ alkyl, $C_1$-$C_2$ perfluoroalkyl, $C_1$-$C_4$ alkoxy, ($C_1$-$C_4$ alkoxy)$C_1$-$C_4$ alkyl, cyclopentyl, cyclohexyl, amino, mono ($C_1$-$C_4$)alkylamino, di($C_1$-$C_4$)alkylamino, unsubstituted or substituted aryl, where aryl is phenyl or naphthyl, a 5 or 6 member unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;
n is 1 or 2;
$R^3$ is $C_1$-$C_4$ alkyl, unsubstituted or substituted phenyl or unsubstituted or substituted benzyl;
$Z^1$ is a bond or —$CH_2$—;
$R^4$ is $C_1$-$C_6$ alkyl, $C_1$-$C_4$ alkoxy, cyclopentyl, cyclohexyl, unsubstituted or substituted aryl where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted bicyclic heterocyclic group having one or two heteroatoms which are the same or different and which are selected from sulfur, oxygen and nitrogen;
when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;
$R^3$ and $R^4$ can be taken together to afford a cyclopentyl, cyclohexyl or a 9 or 10 membered unsubstituted or substituted hydrocarbyl group; and pharmaceutically acceptable salts and solvates thereof;
provided that when (a-i) $R^3$ is methyl or ethyl; $Z^1$ is a bond; $R^4$ is cyclopentyl, cyclohexyl, unsubstituted or substituted aryl where aryl is phenyl or naphthyl or $R^4$ is thienyl or furyl; and X is prolinyl or azetidinyl-2-carbonyl; or (a-ii) $R^4$—$Z^1$— taken together form methyl or ethyl; $R^3$ is unsubstituted or substituted phenyl; and X is prolinyl or azetidinyl-2-carbonyl; or when (b-i) $R^3$ is methyl or ethyl; $Z^1$ is —($CH_2$)—; $R^4$ is unsubstituted or substituted phenyl; and X is azetidinyl-2-carbonyl; or (b-ii) $R^4$—$Z^1$— taken together form methyl or ethyl; $R^3$ is unsubstituted or substituted benzyl; and X is azetidinyl-2-carbonyl; or further when (c) $R^3$ and $R^4$ are taken together to afford a cyclopentyl or cyclohexyl; and X is prolinyl;

then Z is not hydroxy, $C_1$-$C_4$ alkoxy or $NHR^2$ in which $R^2$ is hydrogen, $C_1$-$C_6$ alkyl or a group

in which $R^5$ is $C_1$-$C_4$ alkyl, $C_1$-$C_2$ perfluoroalkyl or $C_1$-$C_4$ alkoxy.

13. A formulation of claim 12 where
$R^1$ is hydrogen;
Z is —$NHR^2$, where
$R^2$ is

or —$S(O)_n$—$R^5$;
$R^3$ is $C_1$-$C_4$ alkyl;
$R^4$ is unsubstituted or substituted aryl where aryl is phenyl or naphthyl;
$R^5$ is $C_1$-$C_4$ alkyl, $C_1$-$C_4$ alkoxy, a 5 or 6 membered unsubstituted or substituted heterocyclic ring having one or two nitrogen atoms, or a 9 or 10 membered unsubstituted or substituted fused bicyclic heterocyclic group having one or two nitrogen atoms;
n is 1 or 2; or
Z is taken together with $R^3$ to afford an azetidinyl group, a 5 or 6 membered unsubstituted or substituted heterocyclic ring having one or two nitrogen atoms or a 9 or 10 membered unsubstituted or substituted fused bicyclic heterocyclic group having one or two nitrogen atoms; and pharmaceutically acceptable salts and solvates thereof.

14. A formulation of claim 13 where
$R^1$ is hydrogen;
X is prolinyl or azetidinyl-2-carbonyl;
Y is a group

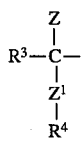

where $R^3$ is $C_1$-$C_4$ alkyl;
$Z^1$ is a bond or $CH_2$—;
$R^4$ is unsubstituted or monosubstituted phenyl; and Z is —NHR², where
R² is

in which R⁵ is a 9 or 10 membered unsubstituted or monosubstituted fused bicyclic heterocyclic group having one nitrogen atom; or R² is a group —SO₂R⁵ in which R⁵ is $C_1$–$C_4$ alkyl; or R³ and Z are taken together to afford an azetidinyl group, or a 5 or 6 membered unsubstituted heterocyclic ring having one or two nitrogen atoms; and pharmaceutically acceptable salts and solvates thereof.

15. A formulation of claim 13 or claim 14 where
R¹ is hydrogen;
Z is —NHR², where
R² is

R³ is $C_1$–$C_4$ alkyl;
Z¹ is —CH₂—;
R⁴ is unsubstituted or monosubstituted phenyl;
R⁵ is $C_1$–$C_4$ alkoxy, or a 9 or 10 membered unsubstituted or monosubstituted fused bicyclic heterocylic group having one nitrogen atom; and pharmaceutically acceptable salts and solvates thereof.

16. A formulation of claim 14 where
R¹ is hydrogen;
Z is —NHR², where
R² is —SO₂R⁵;
R³ is $C_1$–$C_4$ alkyl
R⁴ is unsubstituted or monosubstituted phenyl;
R⁵ is $C_1$–$C_4$ alkyl; and pharmaceutically acceptable salts and solvates thereof.

17. A formulation of claim 14 where
R¹ is hydrogen;
Z is —NHR²;
R⁴ is unsubstituted or monosubstituted phenyl; and
R³ and Z are taken together to afford an azetidinyl group, or a 5 or 6 membered unsubstituted heterocyclic ring having one or two nitrogen atoms; and pharmaceutically acceptable salts and solvates thereof.

18. A formulation of claim 14 where said compound is 1-methylindolyl-2-carbonyl-D-(αmethyl)phenylglycine-L-azetidinyl-2-carbonyl-L-arginine aldehyde and pharmaceutically acceptable salts and solvates thereof.

19. A formulation of claim 14 where said compound is N-ethoxycarbonyl-D-phenylalanyl(αmethyl)-L-prolinyl-L-arginine aldehyde and pharmaceutically acceptable salts and solvates thereof.

20. A formulation of claim 16 where said compound is N-ethylsulfonyl-(D,L)-phenylglycinyl(αmethyl)-L-prolinyl-L-arginine aldehyde and pharmaceutically acceptable salts and solvates thereof.

21. A formulation of claim 17 where said compound is prolinyl(αbenzyl)-L-prolinyl-L-arginine aldehyde and pharmaceutically acceptable salts and solvates thereof.

22. A formulation of claim 17 where said compound is azetidinyl(αbenzyl)-L-prolinyl-L-arginine aldehyde and pharmaceutically acceptable salts and solvates thereof.

23. A method of inhibiting thrombin in mammals, comprising administering to a mammal requiring thrombin inhibition, an effective dose of a compound having the formula

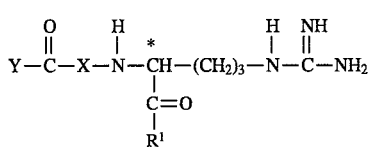

where
R¹ is hydrogen;
X is prolinyl or azetidinyl-2-carbonyl;
Y is a group

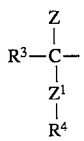

where Z is hydroxy, $C_1$–$C_4$ alkoxy or —NHR²;
R² is hydrogen, $C_1$–$C_6$ alkyl, cyclopentyl, cyclohexyl, a group

or —S(O)ₙ—R⁵
where R⁵ is $C_1$–$C_4$ alkyl, $C_1$–$C_2$ perfluoroalkyl, $C_1$–$C_4$ alkoxy, ($C_1$–$C_4$ alkoxy)$C_1$–$C_4$ alkyl, cyclopentyl, cyclohexyl, amino, mono ($C_1$–$C_4$)alkylamino, di($C_1$–$C_4$)alkylamino, unsubstituted or substituted aryl, where aryl is phenyl or naphthyl, a 5 or 6 member unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;

n is 1 or 2;
R³ is $C_1$–$C_4$ alkyl, unsubstituted or substituted phenyl or unsubstituted or substituted benzyl;
Z¹ is a bond or —CH₂—;
R⁴ is $C_1$–$C_6$ alkyl, $C_1$–$C_4$ alkoxy, cyclopentyl, cyclohexyl, unsubstituted or substituted aryl where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted bicyclic heterocyclic group having one or two heteroatoms which are the same or different and which are selected from sulfur, oxygen and nitrogen;

when Z is —NHR², it can be taken together with R³ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

R³ and R⁴ can be taken together to afford a cyclopentyl, cyclohexyl or a 9 or 10 membered unsubstituted or substituted hydrocarbyl group; and pharmaceutically acceptable salts and solvates thereof;

provided that when (a-i) $R^3$ is methyl or ethyl; $Z^1$ is a bond; $R^4$ is cyclopentyl, cyclohexyl, unsubstituted or substituted aryl where aryl is phenyl or naphthyl or $R^4$ is thienyl or furyl; and x is prolinyl or azetidinyl-2-carbonyl; or (a-ii) $R^4$—$Z^1$— taken together form methyl or ethyl; $R^3$ is unsubstituted or substituted phenyl; and X is prolinyl or azetidinyl-2-carbonyl; or when (b-i) $R^3$ is methyl or ethyl; $Z^1$ is —(CH$_2$)—; $R^4$ is unsubstituted or substituted phenyl; and X is azetidinyl-2-carbonyl; or (b-ii) $R^4$—$Z^1$— taken together form methyl or ethyl; $R^3$ is unsubstituted or substituted benzyl; and X is azetidinyl-2-carbonyl; or further when (c) $R^3$ and $R^4$ are taken together to afford a cyclopentyl or cyclohexyl; and X is prolinyl;

then Z is not hydroxy, $C_1$–$C_4$ alkoxy or $NHR^2$ in which $R^2$ is hydrogen, $C_1$–$C_6$ alkyl or a group

in which $R^5$ is $C_1$–$C_4$ alkyl, $C_1$–$C_2$ perfluoroalkyl or $C_1$–$C_4$ alkoxy.

24. The method of claim 23 where
$R^1$ is hydrogen;
Z is —$NHR^2$, where
$R^2$ is

or —S(O)$_n$—$R^5$;
$R^3$ is $C_1$–$C_4$ alkyl;
$R^4$ is unsubstituted or substituted aryl where aryl is phenyl or naphthyl;
$R^5$ is $C_1$–$C_4$ alkyl, $C_1$–$C_4$ alkoxy, a 5 or 6 membered unsubstituted or substituted heterocyclic ring having one or two nitrogen atoms, or a 9 or 10 membered unsubstituted or substituted fused bicyclic heterocyclic group having one or two nitrogen atoms;
n is 1 or 2; or
Z is taken together with $R^3$ to afford an azetidinyl group, a 5 or 6 membered unsubstituted or substituted heterocyclic ring having one or two nitrogen atoms or a 9 or 10 membered unsubstituted or substituted fused bicyclic heterocyclic group having one or two nitrogen atoms; and pharmaceutically acceptable salts and solvates thereof.

25. The method of claim 24 where
$R^1$ is hydrogen;
X is prolinyl or azetidinyl-2-carbonyl;
Y is a group

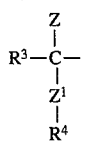

where $R^3$ is $C_1$–$C_4$ alkyl;
$Z^1$ is a bond or $CH_2$—;
$R^4$ is unsubstituted or monosubstituted phenyl; and
Z is —$NHR^2$, where
$R^2$ is

in which $R^5$ is a 9 or 10 membered unsubstituted or monosubstituted fused bicyclic heterocyclic group having one nitrogen atom; or
$R^2$ is a group —$SO_2R^5$ in which $R^5$ is $C_1$–$C_4$ alkyl; or
$R^3$ and Z are taken together to afford an azetidinyl group, or a 5 or 6 membered unsubstituted heterocyclic ring having one or two nitrogen atoms; and pharmaceutically acceptable salts and solvates thereof.

26. The method of claim 24 or claim 25 where
$R^1$ is hydrogen;
Z is —$NHR^2$, where
$R^2$ is

$R^3$ is $C_1$–$C_4$ alkyl;
$Z^1$ is —$CH_2$—;
$R^4$ is unsubstituted or monosubstituted phenyl;
$R^5$ is $C_1$–$C_4$ alkoxy, or a 9 or 10 membered unsubstituted or monosubstituted fused bicyclic heterocylic group having one nitrogen atom; and pharmaceutically acceptable salts and solvates thereof.

27. The method of claim 25 where
$R^1$ is hydrogen;
Z is —$NHR^2$, where
$R^2$ is —$SO_2R^5$;
$R^3$ is $C_1$–$C_4$ alkyl
$R^4$ is unsubstituted or monosubstituted phenyl;
$R^5$ is $C_1$–$C_4$ alkyl; and pharmaceutically acceptable salts and solvates thereof.

28. A method of claim 25 where
$R^1$ is hydrogen;
Z is —$NHR^2$;
$R^4$ is unsubstituted or monosubstituted phenyl; and
$R^3$ and Z are taken together to afford an azetidinyl group, or a 5 or 6 membered unsubstituted heterocyclic ring having one or two nitrogen atoms; and pharmaceutically acceptable salts and solvates thereof.

29. The method of claim 25 where said compound is 1-methylindolyl-2-carbonyl-D-(αmethyl)phenylglycine-L-azetidinyl-2-carbonyl-L-arginine aldehyde and pharmaceutically acceptable salts and solvates thereof.

30. A method of claim 25 where said compound is N-ethoxycarbonyl-D-phenylalanyl(αmethyl)-L-prolinyl-L- arginine aldehyde and pharmaceutically acceptable salts and solvates thereof.

31. A method of claim 27 where said compound is N-ethylsulfonyl-(D,L)-phenylglycinyl(αmethyl)-L-prolinyl-L-arginine aldehyde and pharmaceutically acceptable salts and solvates thereof.

32. A method of claim 28 where said compound is prolinyl(αbenzyl)-L-prolinyl-L-arginine aldehyde and pharmaceutically acceptable salts and solvates thereof.

33. A method of claim 28 where said compound is azetidinyl(αbenzyl)-L-prolinyl-L-arginine aldehyde and pharmaceutically acceptable salts and solvates thereof.

34. A method of treating a thromboembolic disorder comprising administering to a mammal requiring treatment on effective dose of a compound having the formula

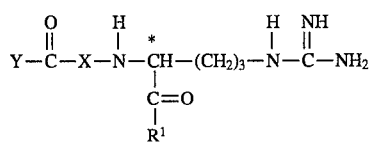

where
$R^1$ is hydrogen;
X is prolinyl or azetidinyl-2-carbonyl;
Y is a group

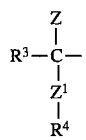

where Z is hydroxy, $C_1$–$C_4$ alkoxy or —$NHR^2$;
$R^2$ is hydrogen, $C_1$–$C_6$ alkyl, cyclopentyl, cyclohexyl a group

or —$S(O)_n$—$R^5$
where $R^5$ is $C_1$–$C_4$ alkyl, $C_1$–$C_2$ perfluoroalkyl, $C_1$–$C_4$ alkoxy, ($C_1$–$C_4$ alkoxy)$C_1$–$C_4$ alkyl, cyclopentyl, cyclohexyl, amino, mono ($C_1$–$C_4$)alkylamino, di($C_1$–$C_4$)alkylamino, unsubstituted or substituted aryl, where aryl is phenyl or naphthyl, a 5 or 6 member unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;
n is 1 or 2;
$R^3$ is $C_1$–$C_4$ alkyl, unsubstituted or substituted phenyl or unsubstituted or substituted benzyl;
$Z^1$ is a bond or —$CH_2$—;
$R^4$ is $C_1$–$C_6$ alkyl, $C_1$–$C_4$ alkoxy, cyclopentyl, cyclohexyl, unsubstituted or substituted aryl where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted bicyclic heterocyclic group having one or two heteroatoms which are the same or different and which are selected from sulfur, oxygen and nitrogen;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted hydrocarbyl group; and pharmaceutically acceptable salts and solvates thereof;

provided that when (a-i) $R^3$ is methyl or ethyl; $Z^1$ is a bond; $R^4$ is cyclopentyl, cyclohexyl, unsubstituted or substituted aryl where aryl is phenyl or naphthyl or $R^4$ is thienyl or furyl; and X is prolinyl or azetidinyl-2-carbonyl; or (a-ii) $R^4$—$Z^1$— taken together form methyl or ethyl; $R^3$ is unsubstituted or substituted phenyl; and x is prolinyl or azetidinyl-2-carbonyl; or when (b-i) $R^3$ is methyl or ethyl; $Z^1$ is —($CH_2$)—; $R^4$ is unsubstituted or substituted phenyl; and X is azetidinyl-2-carbonyl; or (b-ii) $R^4$—$Z^1$— taken together form methyl or ethyl; $R^3$ is unsubstituted or substituted benzyl; and X is azetidinyl-2-carbonyl; or further when (c) $R^3$ and $R^4$ are taken together to afford a cyclopentyl or cyclohexyl; and X is prolinyl;

then Z is not hydroxy, $C_1$–$C_4$ alkoxy or $NHR^2$ in which $R^2$ is hydrogen $C_1$–$C_6$ alkyl or a group

in which $R^5$ is $C_1$–$C_4$ alkyl, $C_1$–$C_2$ perfluoroalkyl or $C_1$–$C_4$ alkoxy.

35. The method of claim 34 where
$R^1$ is hydrogen;
Z is —$NHR^2$, where
$R^2$ is

or —$S(O)_n$—$R^5$;
$R^3$ is $C_1$–$C_4$ alkyl;
$R^4$ is unsubstituted or substituted aryl where aryl is phenyl or naphthyl;
$R^5$ is $C_1$–$C_4$ alkyl, $C_1$–$C_4$ alkoxy, a 5 or 6 membered unsubstituted or substituted heterocyclic ring having one or two nitrogen atoms, or a 9 or 10 membered unsubstituted or substituted fused bicyclic heterocyclic group having one or two nitrogen atoms;
n is 1 or 2; or
Z is taken together with $R^3$ to afford an azetidinyl group, a 5 or 6 membered unsubstituted or substituted heterocyclic ring having one or two nitrogen atoms or a 9 or 10 membered unsubstituted or substituted fused bicyclic heterocyclic group having one or two nitrogen atoms; and pharmaceutically acceptable salts and solvates thereof.

36. The method of claim 35 where
R$^1$ is hydrogen;
X is prolinyl or azetidinyl-2-carbonyl;
Y is a group

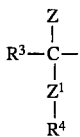

where R$^3$ is C$_1$–C$_4$ alkyl;
Z$^1$ is a bond or CH$_2$—;
R$^4$ is unsubstituted or monosubstituted phenyl; and
Z is —NHR$^2$, where
R$^2$ is

in which R$^5$ is a 9 or 10 membered unsubstituted or monosubstituted fused bicyclic heterocyclic group having one nitrogen atom; or
R$^2$ is a group —SO$_2$R$^5$ in which R$^5$ is C$_1$–C$_4$ alkyl; or
R$^3$ and Z are taken together to afford an azetidinyl group, or a 5 or 6 membered unsubstituted heterocyclic ring having one or two nitrogen atoms; and pharmaceutically acceptable salts and solvates thereof.

37. The method of claim 35 or claim 36 where
R$^1$ is hydrogen;
Z is —NHR$^2$, where
R$^2$ is

R$^3$ is C$_1$–C$_4$ alkyl;
Z$^1$ is —CH$_2$—;
R$^4$ is unsubstituted or monosubstituted phenyl;
R$^5$ is C$_1$–C$_4$ alkoxy, or a 9 or 10 membered unsubstituted or monosubstituted fused bicyclic heterocylic group having one nitrogen atom; and pharmaceutically acceptable salts and solvates thereof.

38. The method of claim 36 where
R$^1$ is hydrogen;
Z is —NHR$^2$, where
R$^2$ is —SO$_2$R$^5$;
R$^3$ is C$_1$–C$_4$ alkyl
R$^4$ is unsubstituted or monosubstituted phenyl;
R$^5$ is C$_1$–C$_4$ alkyl; and pharmaceutically acceptable salts and solvates thereof.

39. The method of claim 36 where
R$^1$ is hydrogen;
Z is —NHR$^2$;
R$^4$ is unsubstituted or monosubstituted phenyl; and
R$^3$ and Z are taken together to afford an azetidinyl group, or a 5 or 6 membered unsubstituted heterocyclic ring having one or two nitrogen atoms; and pharmaceutically acceptable salts and solvates thereof.

40. The method of claim 36 where said compound is 1-methylindolyl-2-carbonyl-D-(αmethyl)phenylglycine-L-azetidinyl-2-carbonyl-L-arginine aldehyde and pharmaceutically acceptable salts and solvates thereof.

41. The method of claim 36 where said compound is N-ethoxycarbonyl-D-phenylalanyl(αmethyl)-L-prolinyl-L-arginine aldehyde and pharmaceutically acceptable salts and solyates thereof.

42. The method of claim 38 where said compound is N-ethylsulfonyl-(D,L)-phenylglycinyl(αmethyl)-L-prolinyl-L-arginine aldehyde and pharmaceutically acceptable salts and solvates thereof.

43. The method of claim 39 where said compound is prolinyl(αbenzyl)-L-prolinyl-L-arginine aldehyde and pharmaceutically acceptable salts and solvates thereof.

44. The method of claim 36 where said compound is azetidinyl(αbenzyl)-L-prolinyl-L-arginine aldehyde and pharmaceutically acceptable salts and solyates thereof.

45. A method of inhibiting coagulation in mammals comprising administering to a mammal requiring coagulation inhibition, an effective dose of a compound having the formula

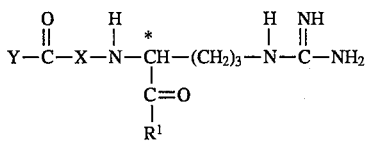

where
R$^1$ is hydrogen;
X is prolinyl or azetidinyl-2-carbonyl;
Y is a group

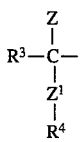

where Z is hydroxy, C$_1$–C$_4$ alkoxy or —NHR$^2$;
R$^2$ is hydrogen, C$_1$–C$_6$ alkyl, cyclopentyl, cyclohexyl, a group

or —S(O)$_n$—R$^5$
where R$^5$ is C$_1$–C$_4$ alkyl, C$_1$–C$_2$ perfluoroalkyl, C$_1$–C$_4$ alkoxy, (C$_1$–C$_4$ alkoxy)C$_1$–C$_4$ alkyl, cyclopentyl, cyclohexyl, amino, mono (C$_1$–C$_4$)alkylamino, di(C$_1$–C$_4$)alkylamino, unsubstituted or substituted aryl, where aryl is phenyl or naphthyl, a 5 or 6 member unsubstituted or substituted heterocyclic ring, having one or two heteroatoms which are the same or different and which are selected from sulfur, oxygen and nitrogen, or a 9 or 10 membered unsubstituted or substituted fused bicyclic heterocyclic group having one or two heteroatoms which are the same or different and which are selected from sulfur, oxygen and nitrogen;
n is 1 or 2;
R$^3$ is C$_1$–C$_4$ alkyl, unsubstituted or substituted phenyl or unsubstituted or substituted benzyl;
Z$^1$ is a bond or —CH$_2$—;

$R^4$ is $C_1$–$C_6$ alkyl, $C_1$–$C_4$ alkoxy, cyclopentyl, cyclohexyl, unsubstituted or substituted aryl where aryl is phenyl or naphthyl, a 5 or 6 membered unsubstituted or substituted heterocyclic ring, having one or two heteroatoms which are the same or different and which are selected from sulfur, oxygen and nitrogen, or a 9 or 10 membered unsubstituted or substituted bicyclic heterocyclic group having one or two heteroatoms which are the same or different and which are selected from sulfur, oxygen and nitrogen;

when Z is —$NHR^2$, it can be taken together with $R^3$ to afford an azetidinyl group, a 5 or 6 membered unsubstituted or substituted saturated nitrogen containing heterocyclic ring or a 9 or 10 membered unsubstituted or substituted fused bicyclic nitrogen containing heterocyclic group;

$R^3$ and $R^4$ can be taken together to afford a cyclopentyl, cyclohexyl or a 9 or 10 membered unsubstituted or substituted hydrocarbyl group; and pharmaceutically acceptable salts and solvates thereof;

provided that when (a-i) $R^3$ is methyl or ethyl; $Z^1$ is a bond; $R^4$ is cyclopentyl, cyclohexyl, unsubstituted or substituted aryl where aryl is phenyl or naphthyl or $R^4$ is thienyl or furyl; and X is prolinyl or azetidinyl-2-carbonyl; or (a-ii) $R^4$—$Z^1$— taken together form methyl or ethyl; $R^3$ is unsubstituted or substituted phenyl; and X is prolinyl or azetidinyl-2-carbonyl; or when (b-i) $R^3$ is methyl or ethyl; $Z^1$ is —(CH$_2$)—; $R^4$ is unsubstituted or substituted phenyl; and X is azetidinyl-2-carbonyl; or (b-ii) $R^4$—$Z^1$— taken together form methyl or ethyl; $R^3$ is unsubstituted or substituted benzyl; and X is azetidinyl-2-carbonyl; or further when (c) $R^3$ and $R^4$ are taken together to afford a cyclopentyl or cyclohexyl; and X is prolinyl;

then Z is not hydroxy, $C_1$–$C_4$ alkoxy or $NHR^2$ in which $R^2$ is hydrogen, $C_1$–$C_6$ alkyl or a group

in which $R^5$ is $C_1$–$C_4$ alkyl, $C_1$–$C_2$ perfluoroalkyl or $C_1$–$C_4$ alkoxy.

46. The method of claim 45 where
   $R^1$ is hydrogen;
   Z is —$NHR^2$, where
   $R^2$ is

or —$S(O)_n$—$R^5$;
$R^3$ is $C_1$–$C_4$ alkyl;
$R^4$ is unsubstituted or substituted aryl where aryl is phenyl or naphthyl;
$R^5$ is $C_1$–$C_4$ alkyl, $C_1$–$C_4$ alkoxy, a 5 or 6 membered unsubstituted or substituted heterocyclic ring having one or two nitrogen atoms, or a 9 or 10 membered unsubstituted or substituted fused bicyclic heterocyclic group having one or two nitrogen atoms;
n is 1 or 2; or Z is taken together with $R^3$ to afford an azetidinyl group, a 5 or 6 membered unsubstituted or substituted heterocyclic ring having one or two nitrogen atoms or a 9 or 10 membered unsubstituted or substituted fused bicyclic heterocyclic group having one or two nitrogen atoms; and pharmaceutically acceptable salts and solvates thereof.

47. The method of claim 46 where
   $R^1$ is hydrogen;
   X is prolinyl or azetidinyl-2-carbonyl;
   Y is a group

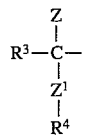

where $R^3$ is $C_1$–$C_4$ alkyl;
$Z^1$ is a bond or $CH_2$—;
$R^4$ is unsubstituted or monosubstituted phenyl; and
Z is —$NHR^2$, where
$R^2$ is

in which $R^5$ is a 9 or 10 membered unsubstituted or monosubstituted fused bicyclic heterocyclic group having one nitrogen atom; or
$R^2$ is a group —$SO_2R^5$ in which $R^5$ is $C_1$–$C_4$ alkyl; or
$R^3$ and Z are taken together to afford an azetidinyl group, or a 5 or 6 membered unsubstituted heterocyclic ring having one or two nitrogen atoms; and pharmaceutically acceptable salts and solvates thereof.

48. The method of claim 46 or claim 47 where
   $R^1$ is hydrogen;
   Z is —$NHR^2$, where
   $R^2$ is

$R^3$ is $C_1$–$C_4$ alkyl;
$Z^1$ is —$CH_2$—;
$R^4$ is unsubstituted or monosubstituted phenyl;
$R^5$ is $C_1$–$C_4$ alkoxy, or a 9 or 10 membered unsubstituted or monosubstituted fused bicyclic heterocylic group having one nitrogen atom; and pharmaceutically acceptable salts and solvates thereof.

49. The method of claim 47 where
   $R^1$ is hydrogen;
   Z is —$NHR^2$, where
   $R^2$ is —$SO_2R^5$;
   $R^3$ is $C_1$–$C_4$ alkyl
   $R^4$ is unsubstituted or monosubstituted phenyl;
   $R^5$ is $C_1$–$C_4$ alkyl; and pharmaceutically acceptable salts and solvates thereof.

50. The method of claim 47 where
   $R^1$ is hydrogen;

Z is —NHR$^2$;

R$^4$ is unsubstituted or monosubstituted phenyl; and

R$^3$ and Z are taken together to afford an azetidinyl group, or a 5 or 6 membered unsubstituted heterocyclic ring having one or two nitrogen atoms; and pharmaceutically acceptable salts and solvates thereof.

51. The method of claim 47 where said compound is 1-methylindolyl-2-carbonyl-D-(αmethyl)phenylglycine-L-azetidinyl-2-carbonyl-L-arginine aldehyde and pharmaceutically acceptable salts and solyates thereof.

52. The method of claim 47 where said compound is N-ethoxycarbonyl-L-phenylalanyl(αmethyl)-L-prolinyl-L-arginine aldehyde and pharmaceutically acceptable salts and solyates thereof.

53. The method of claim 49 where said compound is N-ethylsulfonyl-(D,L)-phenylglycinyl(αmethyl)-L-prolinyl-L-arginine aldehyde and pharmaceutically acceptable salts and solvates thereof.

54. The method of claim 50 where said compound is prolinyl(αbenzyl)-L-prolinyl-L-arginine aldehyde and pharmaceutically acceptable salts and solvates thereof.

55. The method of claim 50 where said compound is azetidinyl(αbenzyl)-L-prolinyl-L-arginine aldehyde and pharmaceutically acceptable salts and solvates thereof.

* * * * *

UNITED STATES PATENT AND TRADEMARK OFFICE
CERTIFICATE OF CORRECTION

PATENT NO.    :  5,484,772

DATED         :  January 16, 1996

INVENTOR(S)   :  Daniel J. Sall, Robert T. Shuman,
                 Gerald F. Smith, and Michael R. Wiley It is certified that an error appears in the above-identified patent and that said Letters Patent is hereby corrected as shown below:

```
At the following locations, please delete "solyate" and insert
--solvateS
Column 49, line 42; column 50, line 26; column 50, line 56; column 52, line
51; column 53, line 15; column 53, line 32; column 53, line 41; Column 53,
line 49; column 53, line 53; column 53, line 57; column 53, line 61; column
55, line 2; column 55, line 62; column 56, line 27; column 57, line 2;
column 57, line 6; column 57, line 8; column 58, line 13; column 58, line
67; column 60, line 8; column 60, line 17; column 61, line 20; column 62,
line 7; column 63, line 10; column 63, line 14.

At column 50, line 12, delete "i" and insert --is-- therefor.

At column 51, line 23, delete "grou" and insert --group-- therefor.

At column 63, line 12, delete "L" and insert --D-- therefor. (1st occurrence)
Column 2,
At "Attorney, Agent, or Firm" on the cover page, delete "Demetery" and
insert --Demeter-- therefor.
```

Signed and Sealed this

Second Day of July, 1996

BRUCE LEHMAN

Attest:

Attesting Officer

Commissioner of Patents and Trademarks